(12) United States Patent
Every et al.

(10) Patent No.: US 7,981,401 B2
(45) Date of Patent: *Jul. 19, 2011

(54) DIURETIC AEROSOLS AND METHODS OF MAKING AND USING THEM

(75) Inventors: Nathan R. Every, Seattle, WA (US); Ron L. Hale, Woodside, CA (US); Amy T. Lu, Los Altos, CA (US); Joshua D. Rabinowitz, Princeton, NJ (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 11/670,892

(22) Filed: Feb. 2, 2007

(65) Prior Publication Data

US 2007/0140982 A1   Jun. 21, 2007

Related U.S. Application Data

(63) Continuation of application No. 10/712,365, filed on Nov. 12, 2003, now abandoned.

(60) Provisional application No. 60/429,123, filed on Nov. 26, 2002.

(51) Int. Cl.

| | | |
|---|---|---|
| *A61K 9/12* | (2006.01) | |
| *A61K 9/00* | (2006.01) | |
| *A61K 31/18* | (2006.01) | |
| *A61K 31/05* | (2006.01) | |
| *A61K 31/20* | (2006.01) | |
| *A61K 31/415* | (2006.01) | |
| *A61K 31/40* | (2006.01) | |
| *A61K 31/50* | (2006.01) | |
| *A61K 31/58* | (2006.01) | |
| *A61K 31/522* | (2006.01) | |

(52) U.S. Cl. ............ 424/43; 424/45; 514/173; 514/249; 514/263.34; 514/404; 514/416; 514/560; 514/601; 514/737

(58) Field of Classification Search ................... 424/43, 424/45; 514/173.249, 263.34, 404, 416, 514/560, 601, 736, 737

See application file for complete search history.

(56) References Cited

U.S. PATENT DOCUMENTS

| | | | |
|---|---|---|---|
| 3,219,533 | A | 11/1965 | Mullins |
| 3,282,729 | A | 11/1966 | Richardson et al. |
| 3,296,249 | A | 1/1967 | Bell |
| 3,299,185 | A | 1/1967 | Oda et al. |
| 3,371,085 | A | 2/1968 | Reeder et al. |
| 3,393,197 | A | 7/1968 | Pachter |
| 3,433,791 | A | 3/1969 | Bentley et al. |
| 3,560,607 | A | 2/1971 | Hartley et al. |
| 3,701,782 | A | 10/1972 | Hester |
| 3,831,606 | A | 8/1974 | Damani |
| 3,864,326 | A | 2/1975 | Babington |
| 3,894,040 | A | 7/1975 | Buzby, Jr. |
| 3,909,463 | A | 9/1975 | Hartman |
| 3,943,941 | A | 3/1976 | Boyd et al. |
| 3,949,743 | A | 4/1976 | Shanbrom |
| 3,971,377 | A | 7/1976 | Damani |
| 3,982,095 | A | 9/1976 | Robinson |
| 3,987,052 | A | 10/1976 | Hester, Jr. |
| 4,008,723 | A | 2/1977 | Borthwick et al. |
| 4,045,156 | A | 8/1977 | Chu et al. |
| 4,079,742 | A | 3/1978 | Rainer et al. |
| 4,096,868 | A | 6/1978 | Norman |
| 4,104,210 | A | 8/1978 | Coran et al. |
| 4,121,583 | A | 10/1978 | Chen |
| 4,141,369 | A | 2/1979 | Burruss |
| 4,160,765 | A | 7/1979 | Weinstock |
| 4,164,950 | A | 8/1979 | Bechtold |
| 4,166,087 | A | 8/1979 | Cline et al. |
| 4,183,912 | A | 1/1980 | Rosenthale |
| 4,190,654 | A | 2/1980 | Gherardi et al. |
| 4,198,200 | A | 4/1980 | Fonda et al. |
| RE30,285 | E | 5/1980 | Babington |
| 4,219,031 | A | 8/1980 | Rainer et al. |

(Continued)

FOREIGN PATENT DOCUMENTS

DE     561 103     1/1928

(Continued)

OTHER PUBLICATIONS

Gottlieb, S.S. "Renal effects of adenosine A1-receptor antagonists in congestive heart failure," Drugs, 2001, 61(10), Abstract only.*

(Continued)

*Primary Examiner* — James H Alstrum Acevedo
(74) *Attorney, Agent, or Firm* — Swanson & Bratschun, L.L.C.

(57) ABSTRACT

Described herein are diuretic condensation aerosols and methods of making and using them. Kits for delivering a condensation aerosol are also described. The diuretic aerosols typically comprise diuretic condensation aerosol particles that comprise a diuretic compound. In some variations the diuretic compound is selected from the group consisting of bumetanide, ethacrynic acid, furosemide, muzolimine, spironolactone, torsemide, triamterene, tripamide, BG 9928, and BG 9719. Methods of treating edema using the described aerosols are also provided. In general, the methods typically comprise the step of administering a therapeutically effective amount of diuretic condensation aerosol to a person with edema. The diuretic condensation aerosol may be administered in a single inhalation, or may be administered in more than one inhalation. Methods of forming a diuretic condensation aerosol are also described. The methods typically comprise the steps of providing a diuretic composition, vaporizing the composition to form a vapor, and then condensing the diuretic composition vapor.

109 Claims, 4 Drawing Sheets

U.S. PATENT DOCUMENTS

| | | |
|---|---|---|
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,484,577 A | 11/1984 | Sackner et al. |
| 4,508,726 A | 4/1985 | Coleman |
| 4,523,589 A | 6/1985 | Krauser |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,654,370 A | 3/1987 | Marriott, III et al. |
| 4,683,231 A | 7/1987 | Glassman |
| 4,693,868 A | 9/1987 | Katsuda et al. |
| 4,708,151 A | 11/1987 | Shelar |
| 4,714,082 A | 12/1987 | Banerjee et al. |
| 4,734,560 A | 3/1988 | Bowen |
| 4,735,217 A | 4/1988 | Gerth et al. |
| 4,735,358 A | 4/1988 | Morita et al. |
| 4,750,483 A | 6/1988 | Ankartross et al. |
| 4,753,758 A | 6/1988 | Miller |
| 4,755,508 A | 7/1988 | Bock et al. |
| 4,756,318 A | 7/1988 | Clearman et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,849,181 A | 7/1989 | Kelley et al. |
| 4,852,561 A | 8/1989 | Sperry |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,895,719 A | 1/1990 | Radhakrishnan et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A | 5/1990 | Brooks et al. |
| 4,924,883 A | 5/1990 | Perfetti et al. |
| 4,928,714 A | 5/1990 | Shannon |
| 4,941,483 A | 7/1990 | Ridings et al. |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz et al. |
| 5,042,509 A | 8/1991 | Banerjee et al. |
| 5,049,389 A | 9/1991 | Radhakrishnan |
| 5,060,666 A | 10/1991 | Clearman et al. |
| 5,060,667 A | 10/1991 | Strubel |
| 5,060,671 A | 10/1991 | Counts et al. |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,093,894 A | 3/1992 | Deevi et al. |
| 5,095,921 A | 3/1992 | Losee et al. |
| 5,099,861 A | 3/1992 | Clearman et al. |
| 5,105,831 A | 4/1992 | Banerjee et al. |
| 5,112,598 A | 5/1992 | Biesalski |
| 5,118,494 A | 6/1992 | Schultz et al. |
| 5,119,834 A | 6/1992 | Shannon et al. |
| 5,126,123 A | 6/1992 | Johnson |
| 5,133,368 A | 7/1992 | Neumann et al. |
| 5,135,009 A | 8/1992 | Muller et al. |
| 5,137,034 A | 8/1992 | Perfetti et al. |
| 5,144,962 A | 9/1992 | Counts et al. |
| 5,146,915 A | 9/1992 | Montgomery |
| 5,156,170 A | 10/1992 | Clearman et al. |
| 5,160,664 A | 11/1992 | Liu |
| 5,164,740 A | 11/1992 | Ivri |
| 5,166,202 A | 11/1992 | Schweizer |
| 5,167,242 A | 12/1992 | Turner et al. |
| 5,177,071 A | 1/1993 | Freidinger et al. |
| 5,182,300 A * | 1/1993 | Pellegata ..................... 514/471 |
| 5,186,164 A | 2/1993 | Raghuprasad |
| 5,192,548 A | 3/1993 | Velasquez et al. |
| 5,224,498 A | 7/1993 | Deevi et al. |
| 5,229,120 A | 7/1993 | DeVincent |
| 5,229,382 A | 7/1993 | Chakrabarti et al. |
| 5,240,922 A | 8/1993 | O'Neill |
| 5,247,949 A | 9/1993 | Deevi et al. |
| 5,249,586 A | 10/1993 | Morgan et al. |
| 5,264,433 A | 11/1993 | Sato et al. |
| 5,284,133 A | 2/1994 | Burns et al. |
| 5,292,499 A | 3/1994 | Evans et al. |
| 5,293,865 A | 3/1994 | Altner et al. |
| 5,322,075 A | 6/1994 | Deevi et al. |
| 5,333,106 A | 7/1994 | Lanpher et al. |
| 5,345,951 A | 9/1994 | Serrano et al. |
| 5,364,838 A | 11/1994 | Rubsamen |
| 5,366,770 A | 11/1994 | Wang |
| 5,372,127 A | 12/1994 | Thwaites et al. |
| 5,376,386 A | 12/1994 | Ganderton et al. |
| 5,381,487 A | 1/1995 | Shamos |
| 5,388,574 A | 2/1995 | Ingebrethsen |
| 5,391,081 A | 2/1995 | Lampotang et al. |
| 5,399,574 A | 3/1995 | Robertson et al. |
| 5,400,808 A | 3/1995 | Turner et al. |
| 5,408,574 A | 4/1995 | Deevi et al. |
| 5,419,315 A | 5/1995 | Rubsamen |
| 5,436,230 A | 7/1995 | Soudant et al. |
| 5,451,408 A | 9/1995 | Mezei et al. |
| 5,455,043 A | 10/1995 | Fischel-Ghodsian |
| 5,456,247 A | 10/1995 | Shilling et al. |
| 5,456,677 A | 10/1995 | Spector |
| 5,457,100 A | 10/1995 | Daniel |
| 5,457,101 A | 10/1995 | Greenwood et al. |
| 5,459,137 A | 10/1995 | Andrasi et al. |
| 5,462,740 A | 10/1995 | Evenstad et al. |
| 5,468,936 A | 11/1995 | Deevi et al. |
| 5,479,948 A | 1/1996 | Counts et al. |
| 5,501,236 A | 3/1996 | Hill et al. |
| 5,507,277 A | 4/1996 | Rubsamen et al. |
| 5,511,726 A | 4/1996 | Greenspan et al. |
| 5,519,019 A | 5/1996 | Andrasi et al. |
| 5,521,357 A | 5/1996 | Lock et al. |
| 5,522,385 A | 6/1996 | Lloyd et al. |
| 5,525,329 A | 6/1996 | Snyder et al. |
| 5,540,959 A | 7/1996 | Wang |
| 5,543,434 A | 8/1996 | Weg |
| 5,544,646 A | 8/1996 | Lloyd et al. |
| 5,547,616 A | 8/1996 | Dancs et al. |
| 5,560,353 A | 10/1996 | Willemot et al. |
| 5,564,442 A | 10/1996 | MacDonald et al. |
| 5,584,701 A | 12/1996 | Lampotang et al. |
| 5,586,550 A | 12/1996 | Ivri et al. |
| 5,591,409 A | 1/1997 | Watkins |
| 5,592,934 A | 1/1997 | Thwaites |
| 5,593,390 A | 1/1997 | Castellano et al. |
| 5,605,146 A | 2/1997 | Sarela |
| 5,605,897 A | 2/1997 | Beasley, Jr. et al. |
| 5,607,691 A | 3/1997 | Hale et al. |

| Patent | Date | Inventor |
|---|---|---|
| 5,613,505 A | 3/1997 | Campbell et al. |
| 5,619,984 A | 4/1997 | Hodson et al. |
| 5,622,944 A | 4/1997 | Hale et al. |
| 5,627,178 A | 5/1997 | Chakrabarti et al. |
| 5,649,554 A | 7/1997 | Sprinkel et al. |
| 5,655,523 A | 8/1997 | Hodson et al. |
| 5,656,255 A | 8/1997 | Jones |
| 5,660,166 A | 8/1997 | Lloyd et al. |
| 5,666,977 A | 9/1997 | Higgins et al. |
| 5,690,809 A | 11/1997 | Subramaniam et al. |
| 5,694,919 A | 12/1997 | Rubsamen et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,767,117 A | 6/1998 | Moskowitz |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,855,564 A | 1/1999 | Ruskewicz |
| 5,855,913 A | 1/1999 | Hanes et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,900,416 A | 5/1999 | Markson |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson et al. |
| 5,928,520 A | 7/1999 | Haumesser |
| 5,929,093 A | 7/1999 | Pang et al. |
| 5,934,272 A | 8/1999 | Lloyd et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,993,748 A | 11/1999 | Wheeler |
| 5,993,805 A | 11/1999 | Sutton et al. |
| 5,997,848 A | 12/1999 | Patton et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,012,450 A | 1/2000 | Rubsamen |
| 6,013,050 A | 1/2000 | Bellhouse et al. |
| 6,014,969 A | 1/2000 | Lloyd et al. |
| 6,014,970 A | 1/2000 | Ivri et al. |
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| RE36,744 E | 6/2000 | Goldberg |
| 6,085,740 A | 7/2000 | Ivri et al. |
| 6,089,227 A | 7/2000 | Nilsson |
| 6,089,857 A | 7/2000 | Matsuura et al. |
| 6,090,212 A | 7/2000 | Mahawili |
| 6,090,403 A | 7/2000 | Block et al. |
| 6,095,134 A | 8/2000 | Sievers et al. |
| 6,095,153 A | 8/2000 | Kessler et al. |
| 6,098,620 A | 8/2000 | Lloyd et al. |
| 6,102,036 A | 8/2000 | Slutsky et al. |
| 6,113,795 A | 9/2000 | Subramaniam et al. |
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,567 A | 10/2000 | Gonda et al. |
| 6,131,570 A | 10/2000 | Schuster et al. |
| 6,133,327 A | 10/2000 | Kimura et al. |
| 6,135,369 A | 10/2000 | Prendergast et al. |
| 6,136,295 A | 10/2000 | Edwards et al. |
| 6,138,683 A | 10/2000 | Hersh et al. |
| 6,140,323 A | 10/2000 | Ellinwood, Jr. et al. |
| 6,143,277 A | 11/2000 | Ashurst et al. |
| 6,143,746 A | 11/2000 | Daugan et al. |
| 6,148,815 A | 11/2000 | Wolf |
| 6,149,892 A | 11/2000 | Britto |
| 6,155,268 A | 12/2000 | Takeuchi |
| 6,158,431 A | 12/2000 | Poole |
| 6,164,287 A | 12/2000 | White |
| 6,167,880 B1 | 1/2001 | Gonda et al. |
| 6,182,892 B1 | 2/2001 | Angelo et al. |
| 6,190,326 B1 | 2/2001 | McKinnon et al. |
| 6,225,890 B1 | 5/2001 | Murphy |
| 6,234,167 B1 | 5/2001 | Cox et al. |
| 6,241,969 B1 | 6/2001 | Saidi et al. |
| 6,246,994 B1 | 6/2001 | Wolven et al. |
| 6,255,334 B1 | 7/2001 | Sands |
| 6,263,872 B1 | 7/2001 | Schuster et al. |
| 6,264,922 B1 | 7/2001 | Wood et al. |
| 6,284,287 B1 | 9/2001 | Sarlikiotis et al. |
| 6,299,900 B1 | 10/2001 | Reed et al. |
| 6,306,431 B1 | 10/2001 | Zhang et al. |
| 6,313,176 B1 | 11/2001 | Ellinwood, Jr. et al. |
| 6,376,550 B1 | 4/2002 | Raber et al. |
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,461,591 B1 | 10/2002 | Keller et al. |
| 6,506,762 B1 | 1/2003 | Horvath et al. |
| 6,514,482 B1 | 2/2003 | Bartus et al. |
| 6,516,796 B1 | 2/2003 | Cox et al. |
| 6,591,839 B2 | 7/2003 | Meyer et al. |
| 6,632,047 B2 | 10/2003 | Vinegar et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,776,978 B2 | 8/2004 | Zaffaroni et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |

| | | |
|---|---|---|
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,581,540 B2 * | 9/2009 | Hale et al. ............... 128/203.27 |
| 2001/0020147 A1 | 9/2001 | Staniforth et al. |
| 2001/0039262 A1 | 11/2001 | Venkataraman |
| 2002/0031480 A1 | 3/2002 | Peart et al. |
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0086852 A1 | 7/2002 | Cantor et al. |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0015197 A1 | 1/2003 | Hale et al. |
| 2003/0032638 A1 | 2/2003 | Kim et al. |
| 2003/0051728 A1 | 3/2003 | Lloyd et al. |
| 2003/0062042 A1 | 4/2003 | Wensley et al. |
| 2003/0118512 A1 | 6/2003 | Shen |
| 2003/0131843 A1 | 7/2003 | Lu |
| 2003/0138508 A1 | 7/2003 | Novack et al. |
| 2003/0209240 A1 | 11/2003 | Hale et al. |
| 2004/0009128 A1 | 1/2004 | Rabinowitz et al. |
| 2004/0016427 A1 | 1/2004 | Byron et al. |
| 2004/0096402 A1 | 5/2004 | Hodges et al. |
| 2004/0099266 A1 | 5/2004 | Cross et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0105819 A1 | 6/2004 | Hale et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2005/0258159 A1 | 11/2005 | Hale et al. |
| 2005/0268911 A1 | 12/2005 | Cross et al. |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0153779 A1 | 7/2006 | Rabinowitz et al. |
| 2006/0177382 A1 | 8/2006 | Rabinowitz et al. |
| 2006/0193788 A1 | 8/2006 | Hale et al. |
| 2006/0216243 A1 | 9/2006 | Rabinowitz et al. |
| 2006/0216244 A1 | 9/2006 | Rabinowitz et al. |
| 2006/0233717 A1 | 10/2006 | Hale et al. |
| 2006/0233718 A1 | 10/2006 | Rabinowitz et al. |
| 2006/0233719 A1 | 10/2006 | Rabinowitz et al. |
| 2006/0239936 A1 | 10/2006 | Rabinowitz et al. |
| 2006/0246011 A1 | 11/2006 | Rabinowitz et al. |
| 2006/0246012 A1 | 11/2006 | Rabinowitz et al. |
| 2006/0251587 A1 | 11/2006 | Rabinowitz et al. |
| 2006/0251588 A1 | 11/2006 | Rabinowitz et al. |
| 2006/0257328 A1 | 11/2006 | Rabinowitz |
| 2006/0257329 A1 | 11/2006 | Rabinowitz et al. |
| 2006/0269486 A1 | 11/2006 | Rabinowitz et al. |
| 2006/0269487 A1 | 11/2006 | Rabinowitz et al. |
| 2006/0280692 A1 | 12/2006 | Rabinowitz et al. |
| 2006/0286042 A1 | 12/2006 | Rabinowitz et al. |
| 2006/0286043 A1 | 12/2006 | Rabinowitz et al. |
| 2007/0014737 A1 | 1/2007 | Rabinowitz et al. |
| 2007/0028916 A1 | 2/2007 | Hale et al. |
| 2007/0031340 A1 | 2/2007 | Hale et al. |
| 2007/0122353 A1 | 5/2007 | Hale et al. |
| 2007/0140982 A1 | 6/2007 | Every et al. |
| 2007/0178052 A1 | 8/2007 | Rabinowitz et al. |
| 2007/0286816 A1 | 12/2007 | Hale et al. |
| 2008/0110872 A1 | 5/2008 | Hale et al. |
| 2008/0175796 A1 | 7/2008 | Rabinowitz et al. |
| 2008/0216828 A1 | 9/2008 | Wensley et al. |

FOREIGN PATENT DOCUMENTS

| | | |
|---|---|---|
| DE | 198 54 007 | 5/2000 |
| EP | 0 358 114 | 3/1990 |
| EP | 0 430 559 | 6/1991 |
| EP | 0 492 485 | 7/1992 |
| EP | 0 606 486 | 7/1994 |
| EP | 0 734 719 | 2/1996 |
| EP | 0 967 214 | 12/1999 |
| EP | 1 080 720 | 3/2001 |
| EP | 1 177 793 | 2/2002 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |

| | | |
|---|---|---|
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/36574 | 10/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 8/1998 |
| WO | WO 99/04797 | 2/1999 |
| WO | WO 99/11311 | 3/1999 |
| WO | WO 99/16419 | 4/1999 |
| WO | WO 00/00244 | 5/1999 |
| WO | WO 99/24433 | 5/1999 |
| WO | WO 00/27359 | 7/1999 |
| WO | WO 99/37347 | 7/1999 |
| WO | WO 99/37625 | 7/1999 |
| WO | WO 00/27363 | 9/1999 |
| WO | WO 99/44664 | 9/1999 |
| WO | WO 00/28979 | 11/1999 |
| WO | WO 00/29053 | 11/1999 |
| WO | WO 99/55362 | 11/1999 |
| WO | WO 99/59710 | 11/1999 |
| WO | WO 00/29167 | 12/1999 |
| WO | WO 99/64094 | 12/1999 |
| WO | WO 00/00176 | 1/2000 |
| WO | WO 00/00215 | 1/2000 |
| WO | WO 00/35417 | 1/2000 |
| WO | WO 00/38618 | 1/2000 |
| WO | WO 00/44350 | 1/2000 |
| WO | WO 00/19991 | 4/2000 |
| WO | WO 00/44730 | 4/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/80829 | 11/2001 |
| WO | WO 01/95903 | 12/2001 |
| WO | WO 02/00198 | 1/2002 |
| WO | WO 02/24158 | 3/2002 |
| WO | WO 02/056866 | 7/2002 |
| WO | WO 02/094236 | 11/2002 |
| WO | WO 02/094242 | 11/2002 |
| WO | WO 03/037412 | 5/2003 |

OTHER PUBLICATIONS

Lant, A. "Diuretic dugs. Progress in clinical pharmacology." Drugs, 1986, 31 (Suppl. 4), Abstract only.*

Drug Information Handbook (Lexi-Comp, Inc.: Hudson, OH, 1999-2000, pp. 1017-1018, pp. 1028-1029.*

Bastin, R. J. et al. "Salt Selection and Optimisation Procedures for Pharmaceutical New Chemical Entities," Organic Process Research & Development, 2000, 4, 427-435.*

Bennett, R. L. et al. (1981). "Patient-Controlled Analgesia: A New Concept of Postoperative Pain Relief," Annual Surg. 195(6):700-705.

Benowitz (1994). "Individual Differences in Nicotine Kinetics and Metabolism in Humans," NIDA Research Monography, 2 pages.

BP: Chemicals Products-Barrier Resins (1999). located at <http://www.bp.com/chemicals/products/product.asp> (visited on Aug. 2, 2001), 8 pages.

Brand, P. et al. (Jun. 2000). "Total Deposition of Therapeutic Particles During Spontaneous and Controlled Inhalations," Journal of Pharmaceutical Sciences. 89(6):724-731.

Campbell, Fiona A. et al. (2001) "Are cannabinoids an effective and safe treatment option in the management of pain? A qualitative systemic review," BMJ, 323 pp. 1-6.

Carroll, M.E. et al. (1990), "Cocaine-Base Smoking in Rhesus Monkey: Reinforcing and Physiological Effects," Psychopharmacology (Berl) 102:443-450.

Cichewicz, Diana L. et al. (May 1999) "Enhancement of mu opioid antinociception by oral DELTA 9—tetrahydrocannabinol: Dose response analysis and receptor identification" Journal of Pharmacology and Experimental Therapeutics vol. 289 (2): 859-867.

Clark, A. And Byron, P. (1986). "Dependence of Pulmonary Absorption Kinetics on Aerosol Particle Size," Z. Erkrank. 166:13-24.

Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419- 422.

Darquenne, C. et al. (1997). "Aerosol Dispersion in Human Lung: Comparison Between Numerical Simulations and Experiments for Bolus Tests," American Physiological Society. 966-974.

Database Biosis "Online!" Biosciences Information Service, Philadelphia, PA 1979, Knight, V. et al., "Amantadine aerosol in humans", database accession no. PREV 198069035552 abstract, &Antimicrobial Agents and Chemotherapy 16(5):572-578.

Database Biosis "Online!" Biosciences Information Service, Philadelphia, PA 1979, Wilson. S.Z. et al., "Amatadine Aerosol Particle A.erosol Generation and Delivery to Man" Database accession no. PREV198069008137, abstract & Proceedings of the Society for Experimental Biology and Medicine 161(3):350-354.

Database WPI, Section CH, Week 198941, Derwent Publications Ltd., London, GB; AN 1989-297792 AP002230849 & JP 01 221313 (Nippon Create 1(K), Sep. 4, 1989, abstract.

Davies, C. N. et al. (May 1972). "Breathing of Half-Micron Aerosols," Journal of Applied Physiology. 32(5):591-600.

Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.

Drugs Approved by the FDA-Drug Name: Nicotrol Inhaler (2000) located at <http://www.centerwatch.com/patient/drugs/dru202.html> (Visited on Aug. 2, 2001), 2 pages.

Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.

Finlay, W. H. (2001). "The Mechanics of Inhaled Pharmaceutical Aerosols", Academic Press: San Diego Formula 2.39. pp. 3-14 (Table of Contents). pp. v-viii.

Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.

Graves, D. A. et al. (1983). "Patient-Controlled Analgesia," Annals of Internal Medicine. 99:360-366.

Anonymous, (Jun. 1998) Guidance for Industry: Stability testing of drug substances and products, U.S. Department of Health and Human Services, FDA, CDER, CDER , pp. 1-110.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 μm," J. Aerosol Sci. 17(5):811-822.

Hong et al. (2002) Respiratory Drug Delivery VIII:79-781.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.

James, A.C. et al., (1991). "The Respiratory Tract Deposition Model Proposed by the ICRP Task Group," Radiation Protection Dosimetry, 38(1/3):159-165.

Kim, M. H. and Patel, D.V. (1994). "'BOP' As a Reagent for Mild and Efficient Preparation of Esters," Tet. Letters 35:5603-5606.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Martin, B. R. and Lue, L. P. (May/Jun. 1989). "Pyrolysis and Volatilization of Cocaine," Journal of Analytical Toxicology 13:158-162.

Mattox, a.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Pankow, J. (Mar. 2000). ACS Conference-San Francisco-Mar. 26, 2000. Chemistry of Tobacco Smoke. pp. 1-8.

Poochikian, G. and Bertha, C.M. (2000). "Inhalation Drug Product Excipient Controls: Significance and Pitfalls," Resp. Drug Deliv. VII: 109-115.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

Vapotronics, Inc. (1998) located at Vapotronics, Inc. (1998) located at http://www.vapotronics.com.au/banner.htm., 11 pages, (visited on Jun. 5, 2000).

Vaughan, N. P. (1990). "The Generation of Monodisperse Fibres of Caffeine" J. Aerosol Sci. 21(3): 453-462.

Ward, M. E. Md, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. And Targacept Inc. Announce Alliance to Develop New Drugs to Treat Alzheimer's and Parkinson's Diseases" located at http://www.rpr.spna.com/ABOUT_RPR/pressrels/1999/990209-targa.html (last visited on Jan. 28, 2000) 1 page.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

Wood, R.W. et al. (1996). "Methylecgonidine Coats the Crack Particle" Pharmacology Biochemistry & . Behavior. 53(1):57-66.

Berko et al. (2002) "In vitro and in vivo study in rats of rectal suppositories containing furosemide." European Journal of Pharmaceutics and Biopharmaceutics vol. 53:311-315.

Cavaliere et al. (2002) "Furosemide Protective Effect Against Airway Obstruction." Website www.bentham.org/sample-issues/cdt3-3/cavaliere/cavaliere-ms.htm.

Dormans et al. (1996) "Vascular effects of loop diuretics." Cardiovascular Research 32:988-997.

Faris et al. (2002) "Current evidence supporting the role of diuretics in heart failure: a meta analysis of randomized controlled trials." International Journal of Cardiology vol. 82:149-158.

Iwamoto et al. (2001) "Loop Diuretics and in Vitro Relaxation of Human Fetal and Newborn Mouse Airways." Pediatric Research vol. 50 No. 2: 273-276.

Nielsen et al. (2000) "Intranasal Administration of Different Liquid Formulation of Bumetanide to Rabbits" International Journal of Pharmaceutics 204:35-41.

Nishino et al. (2000) "Inhaled Furosemide Greatly Alleviates the Sensation of Experimentally Induced Dyspnea." Am J Respir Crit Care Med vol. 161: 1963-1967.

O'Connor et al. (1991) "Effect of Inhaled Furosemide and Bumetanide on Adenosine 5'-monophosphate- and sodium metabisulfite-induced bronchoconstriction in asthmatic subjects." Am. Rev. Repir. Dis. 146(6): 1329-33.

U.S. Appl. No. 12/245,184, filed Oct. 3, 2008, Hale et al.
U.S. Appl. No. 12/117,737, filed May 8, 2008, Hale et al.
U.S. Appl. No. 11/964,630, file Dec. 26, 2007, Hale et al.
U.S. Appl. No. 12/211,554, filed Sep. 16, 2008, Sharma et al.
U.S. Appl. No. 12/111,188, filed Apr. 28, 2008, Hale et al.
U.S. Appl. No. 12/211,247, filed Sep. 16, 2008, Sharma et al.
U.S. Appl. No. 12/211,628, filed Sep. 16, 2008, Lei et al.

Pardeep et al. (2000) "The acute vascular effects of frusemide in heart failure." Br J Clin Pharmacol vol. 50:9-13.

Polosa et al. (1993) "Relative Potencies and Time Course of Changes in Adenosine 5'Monophosphate Airway Responsiveness with Inahled Furosemide and Bumetanide in Asthma." J. Allergy Clin. Immunol. 92(2):288-97.

Polosa et al. (1995) "Inhaled Loop Diuretics and Basal Airway Responsiveness in Man: Evidence of a Role for Cyclo-oygenase Products." Eur. Respir. J 8(4):593-599.

Puschett, J.B. "Diuretics and the Therapy of Hypertension," J. Med. Sci., Jan. 2001, Vo. 319(1), pp. 1-9.

Shankar et al. (2003) "Loop diuretics: from the Na-K-2Cl transporter to clinical use." Am J Physiol Renal Pysiol. 283:F11-21.

Shimoyama et al. (2002) "Nebulized Furosemide as a Novel Treatment for Dyspnea in Terminal Cancer Patients." Journal of Pain and Symptom Management vol. 23 No. 1: 73:76.

Solomons, TWG Organic Chemistry, 5th ed. John Wiley & Sons, Inc.: New York, 1992, p. 784.

* cited by examiner

Fig. 4

DIURETIC AEROSOLS AND METHODS OF MAKING AND USING THEM

CROSS REFERENCE TO RELATED APPLICATIONS

This application is a continuation of U.S. application Ser. No. 10/712,365 entitled, "Diuretic Aerosols and Methods of Making and Using Them", filed on Nov. 12, 2003; which claims priority to U.S. Provisional Application Ser. No. 60/429,123 entitled, "Delivery of a Diuretic through an Inhalation Route" filed on Nov. 26, 2002. The above listed applications are hereby incorporated by reference in their entirety.

BACKGROUND

Edema is a localized or general swelling caused by the build-up of fluid within body tissues. It most commonly occurs in the feet and legs, where it also is referred to as peripheral edema. However, excess fluid can occur anywhere in the subcutaneous tissue or lungs. This excess fluid may be the result of any number of causes. For example, it may be the result of poor blood circulation, lymphatic system failure, disease of the heart or kidneys, reduction in the amount of blood protein (e.g., which may occur as a result of cirrhosis), chronic nephritis, malnutrition, or toxemia of pregnancy (preeclampsia). Some other causes of edema are use of birth control pills, premenstrual syndrome, sunburn, and an imbalance of sodium and potassium. Localized edema may also result from injury or infection.

Diuretics are most typically used to treat edema. Some diuretics are used to treat Meniere's disease and other types of vertigo where excessive fluid pressure builds up within the inner ear. Some diuretics are used to treat glaucoma, where excessive fluid pressure builds up within the eyeball. Similarly, some diuretics are used to treat pulmonary edema, where fluid accumulates in the lung tissue. Diuretics may also be used to treat high blood pressure (i.e., hypertension), overdosage of certain drugs, and cystic fibrosis.

There are a number of compositions commercially available as diuretics. These include ethacrynic acid, bumetanide, furosemide, muzolimine, spironolactone, torsemide, triamterene, and tripamide. These diuretics are most commonly delivered as an oral dosage form (e.g. as a pill, capsule, or tablet), or delivered intravenously. Disadvantages of oral dosage forms include a delay in the onset of activity and loss of drug therapeutic effect due to hepatic first-pass metabolism. Intravenous delivery, while typically more effective than oral delivery (particularly for loop diuretics), is often painful and inconvenient. Currently, intravenous delivery is the only option available for exacerbations of congestive heart failure. It would be desirable to provide other dosage forms and routes of administration with improved properties.

SUMMARY

Described herein are diuretic condensation aerosols and methods of making and using them. Kits for delivering a condensation aerosol are also described. The diuretic aerosols described herein typically comprise diuretic condensation aerosol particles, where the particles comprises a diuretic selected from the group consisting of bumetanide, ethacrynic acid, furosemide, muzolimine, spironolactone, torsemide, triamterene, tripamide, BG 9928, and BG 9719. In some variations the diuretic compound is bumetanide.

In some variations, the aerosol comprises at least 50% by weight of diuretic condensation particles. In other variations the aerosol comprises at least 75% or 95% by weight of the diuretic condensation particles. Similarly, in some variations, the aerosol is substantially free of thermal degradation products, and in some variations, the diuretic condensation aerosol has a MMAD in the range of 1-3 µm. In some variations, the diuretic condensation aerosol has a MMAD in the range of 1-3.5 µm.

The kit for delivering a diuretic condensation aerosol typically comprises a composition comprising a diuretic compound, and a device for forming a diuretic aerosol. The device for forming a diuretic aerosol typically comprises an element configured to heat the composition to form a vapor, an element allowing the vapor to condense to form a condensation aerosol, and an element permitting a user to inhale the condensation aerosol. The composition may further comprise a pharmaceutically acceptable excipient, and the device my further comprise features such as breath-actuation or lock-out elements.

Methods of treating edema using the aerosols described herein are also provided. In general, the method comprises the step of administering a therapeutically effective amount of a diuretic condensation aerosol to a person with edema. The edema may be caused or be associated with any number of maladies. For example, the edema may be the result of congestive heart failure, cirrhosis of the liver, poor blood circulation, lymphatic system failure, chronic nephritis, malnutrition, toxemia of pregnancy (preeclampsia), use of birth control pills, premenstrual syndrome, sunburn, hypertension, overdosage of certain drugs, Meniere's disease, glaucoma, cystic fibrosis, and an imbalance of sodium and potassium. Localized edema may also result from injury or infection.

In some variations, the method for treating edema comprising the step of administering a therapeutically effective amount of a diuretic aerosol to a person with edema, wherein the diuretic aerosol comprises a diuretic compound and has a MMAD in the range of about 1-3 µm, and wherein a peak plasma level of at least 30 ng/mL of the diuretic compound is achieved within 10 minutes of administration. In some variations, the method comprises the steps of obtaining a weight measurement of the person with edema prior to the step of administering a therapeutically effective amount of a diuretic aerosol, and using that weight measurement to assess whether to administer a therapeutically effective amount of a diuretic aerosol.

In some variations, the described condensation aerosol has a MMAD in the range of about 1-3 µm. In some variations, the described condensation aerosol has a MMAD in the range of 1-3.5 µm. In some variations, the condensation aerosol comprises a diuretic selected from the group consisting of bumetanide, ethacrynic acid, furosemide, muzolimine, spironolactone, torsemide, triamterene, tripamide, BG 9928, and BG 9719. In some variations the diuretic compound is bumetanide. In other variations, the diuretic achieves a $C_{max}$ within a certain time period after the aerosol is administered. For example, in some variations, the diuretic achieves a $C_{max}$ in 10 minutes or less after the aerosol is administered. The diuretic condensation aerosol may be administered in a single inhalation, or may be administered in more than one inhalation.

Methods of treating congestive heart failure using the aerosols described herein are also provided. In general, the method comprises the step of administering a therapeutically effective amount of a loop diuretic condensation aerosol to a person with congestive heart failure. This method may be particularly useful in treating those symptoms associated with congestive heart failure exacerbations.

In some variations, the method for treating congestive heart failure exacerbation comprising the step of administering a therapeutically effective amount of a loop diuretic aerosol to a person with symptoms of congestive heart failure exacerbation, wherein the loop diuretic aerosol comprises a loop diuretic compound and has a MMAD in the range of about 1-3 μm, and wherein a peak plasma level of at least 30 ng/mL of the loop diuretic compound is achieved within 10 minutes of administration. In other variations, the loop diuretic achieves a $C_{max}$ within a certain time period after the aerosol is administered. For example, in some variations, the loop diuretic achieves a $C_{max}$ in 10 minutes or less after the aerosol is administered. The loop diuretic condensation aerosol may be administered in a single inhalation, or may be administered in more than one inhalation.

Methods of forming a diuretic condensation aerosol are also described. The methods of forming a diuretic condensation aerosol typically comprise the steps of providing a diuretic composition, vaporizing the diuretic composition, and condensing the diuretic composition. The step of vaporizing the diuretic composition typically comprises the step of heating the composition to form a vapor.

The composition typically comprises a diuretic selected from the group consisting of bumetanide, ethacrynic acid, furosemide, muzolimine, spironolactone, torsemide, triamterene, and tripamide, BG 9928, and BG 9719. In some variations the diuretic compound is bumetanide. The diuretic composition may also comprise a pharmaceutically acceptable excipient.

BRIEF DESCRIPTION OF THE DRAWINGS

FIG. 4 is a plot depicting the effects of film thickness on aerosol purity for bumetanide.

DETAILED DESCRIPTION

Definitions

Figure 1:
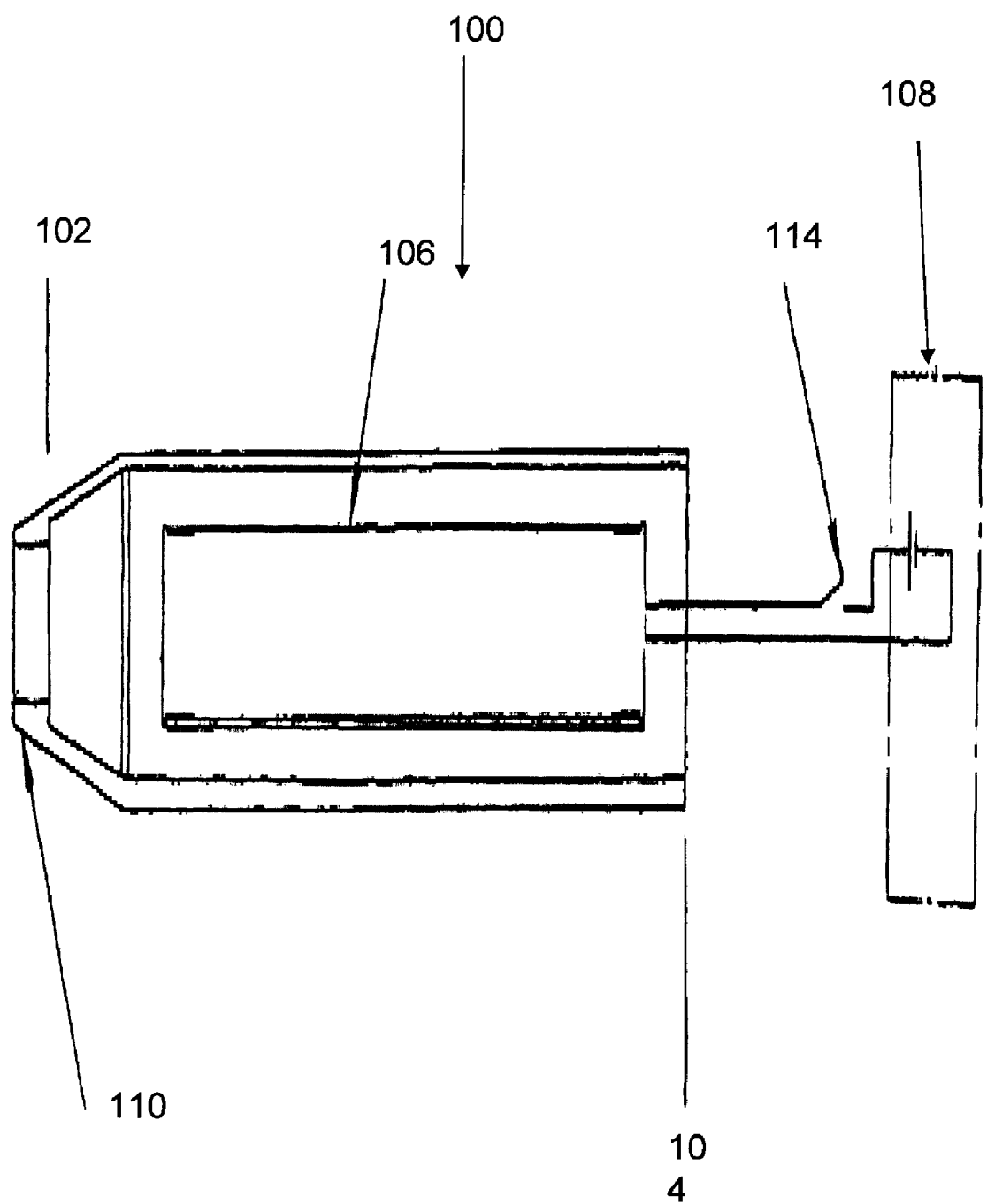
FIG. 1 is an illustration of an exemplary device that may be used to form and administer the aerosols described herein.

As defined herein, the following terms shall have the following meanings when reference is made to them throughout the specification.

"Condensation aerosol" refers to an aerosol that has been formed by the vaporization and subsequent cooling of the vapor, such that the vapor condenses to form particles.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Substantially free of thermal degradation products" means that the aerosol is at least 50% free of thermal degradation products.

"Therapeutically effective amount" means the amount required to achieve a therapeutic effect. The therapeutic effect could be any therapeutic effect ranging from prevention, symptom amelioration, symptom treatment, to disease termination or cure.

"Thermal degradation product" means any byproduct, which results from heating the diuretic composition and is not responsible for producing a therapeutic effect.

"Vapor" refers to a gas, and "vapor phase" refers to a gas phase. The term "thermal vapor" refers to a vapor phase, aerosol, or mixture of aerosol-vapor phases, formed preferably by heating.

Diuretic Compositions

The diuretic compositions described herein typically comprise at least one diuretic compound. The diuretic compositions may comprise other compounds as well. For example, the diuretic composition may comprise a mixture of diuretic compounds, a mixture of a diuretic compound and a pharmaceutically acceptable excipient, or a mixture of a diuretic compound with other compounds having useful or desirable properties. The diuretic composition may comprise a pure diuretic compound as well.

Any suitable diuretic compound may be used. In general, we have found that suitable diuretics have properties that make them acceptable candidates for use with the devices and methods herein described. For example, the diuretic compound is typically one that is, or can be made to be, vaporizable.

Classes of diuretics suitable for use with the described methods and devices include the carbonic anhydrase inhibitors, osmotic diuretics, loop diuretics, thiazide and thiazide-like diuretics, potassium sparing diuretics, and aldosterone antagonists. Exemplary diuretic compounds within these classes include bumetanide, ethacrynic acid, furosemide, muzolimine, spironolactone, torsemide, triamterene, tripamide, BG 9928 (Bicyclo[2,2,2]octane-1-propanoic acid, 4-(2,3,6,7-tetrahydro-2,6-dioxo-1,3-dipropyl-1H-purin-8yl)-(9CI)), and BG 9719 (1H-Purine-2,6-dione, 3,7-dihydro-8-(3-oxatricyclo[3,2,1,02,4]oct-6-yl)-1,3-dipropyl-[1S-(1α, 2β,4β,5α,6β)], and pharmaceutically acceptable analogs and equivalents thereof. A table providing chemical structures and some physical properties for a few of these illustrative compounds is provided below.

TABLE 1

Suitable Diuretic Compounds

Bumetanide
$C_{17}H_{20}N_2O_5S$
Mol. Wt.: 364.4
Log P: 2.61
CLogP: 3.37219

TABLE 1-continued

Suitable Diuretic Compounds

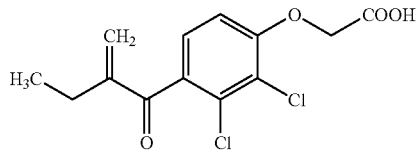

Ethacrynic Acid
$C_{13}H_{12}Cl_2O_4$
Mol. Wt.: 303.1
Log P: 3.05
CLogP: 3.44499

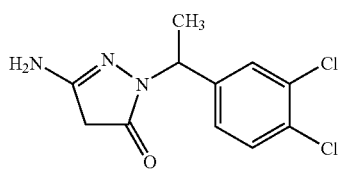

Muzolimine
$C_{11}H_{11}Cl_2N_3O$
Mol. Wt.: 272.1
Log P: 2.18
CLogP: 1.328

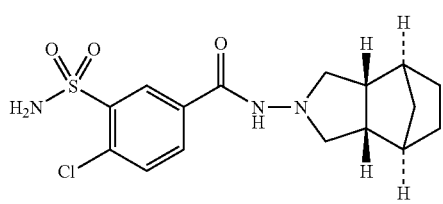

Tripamide
$C_{16}H_{20}ClN_3O_3S$
Mol. Wt.: 369.9
Log P: 1.72
CLogP: 2.47501

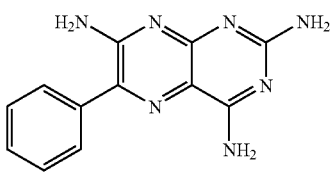

Triamterene
$C_{12}H_{11}N_7$
Mol. Wt.: 253.3
Log P: 2.11
CLogP: 1.60761

TABLE 1-continued

Suitable Diuretic Compounds

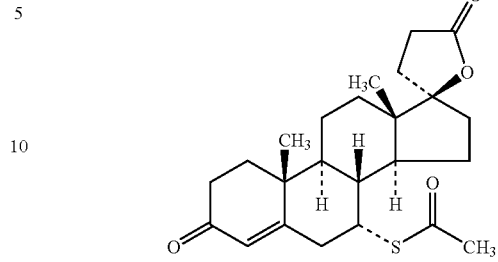

Spironolactone
$C_{24}H_{32}O_4S$
Mol. Wt.: 416.6
Log P: 2.90
CLogP: 2.249

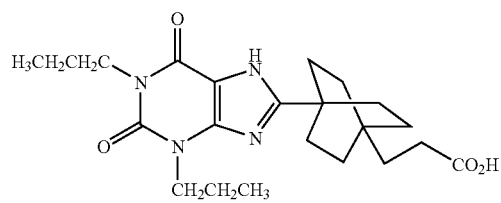

BG-9928
$C_{22}H_{32}N_4O_4$
Mol. Wt.: 416.5
Log P: 3.33
CLogP: 4.6225

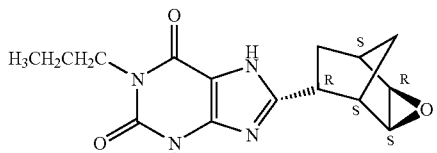

BG-9719
CVT-124
$C_{18}H_{24}N_4O_3$
Mol. Wt.: 344.4
Log P: 1.43
CLogP: 2.5535

Typically, the diuretic compound is in its ester or free acid form. However, it is not without possibility that the diuretic compound will be vaporizable from its salt form. Indeed, a variety of pharmaceutically acceptable salts are suitable for aerosolization. Illustrative salts include, without limitation, the following: sodium, potassium, or other alkali metal salts, and ammonium or substituted ammonium salts. Salt forms of diuretics can be obtained from their corresponding free acid using well known methods in the art.

Suitable pharmaceutically acceptable excipients may be volatile or nonvolatile. Volatile excipients, when heated, are concurrently volatilized, aerosolized and inhaled with the diuretic. Classes of such excipients are known in the art and include, without limitation, gaseous, supercritical fluid, liquid and solid solvents. The following is a list of exemplary carriers within these classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid Support Typically, the diuretic composition is coated on a solid support, and then the solid support is heated to vaporize the diuretic composition. The support may be of any geometry and be of a variety of different sizes. It is often desirable that the solid support provide a large surface to volume ratio (e.g., greater than 100 per meter) and a large surface to mass ratio (e.g., greater than 1 cm$^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials may be used to construct the solid supports. Classes of such materials include, without limitation, metals, inorganic materials, carbonaceous materials, and polymers. Illustrative materials within these classes are aluminum, silver, iron, gold, stainless steel, copper and tungsten; silica, glass, silicon and alumina; graphite, porous carbons, carbon yarns and carbon felts, ceramics; and polytetrafluoroethylene. In one variation, the solid support is stainless steel. Combinations of materials and coated variants of materials may be used as well.

When it is desirable to use aluminum as a solid support, aluminum foil is a suitable material. Examples of silica, alumina and silicon based materials include amphorous silica S-5631 (Sigma, St. Louis, Mo.), BCR171 (an alumina of defined surface area greater than 2 m$^2$/g from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

Typically it is desirable that the solid support have relatively few, or substantially no, surface irregularities. Although a variety of supports may be used, supports that have an impermeable surface, or an impermeable surface coating, are typically desirable. Illustrative examples of such supports include metal foils, smooth metal surfaces, nonporous ceramics, and the like.

The diuretic composition is typically coated on the solid support in the form of a film. The film may be coated on the solid support using any suitable method. The method suitable for coating is often dependent upon the physical properties of the diuretic compound and the desired film thickness. One exemplary method of coating a diuretic composition on a solid support is by preparing a solution of diuretic compound (alone or in combination with other desirable compounds) in a suitable solvent, applying the solution to the exterior surface of the solid support, and then removing the solvent (e.g., via evaporation, etc.) thereby leaving a film on the support surface.

Common solvents include methanol, dichloromethane, methyl ethyl ketone, diethyl ether, 3:1 chloroform:methanol mixture, 1:1 dichloromethane:methyl ethyl ketone mixture, dimethylformamide, and deionized water. In some instances (e.g., when triamterene is used), it is desirable to use a solvent such as formic acid. Sonication may also be used as necessary to dissolve the diuretic compound.

The diuretic composition may also be coated on the solid support by dipping the support into a diuretic composition solution, or by spraying, brushing or otherwise applying the solution to the support. Alternatively, a melt of the drug can be prepared and applied to the support. For drugs that are liquids at room temperature, thickening agents can be mixed with the drug to permit application of a solid drug film.

Formation of Diuretic Condensation Aerosols

Any suitable method may be used to form the condensation aerosols described herein. One such method involves the heating of a diuretic composition to form a vapor, followed by cooling of the vapor so that it forms an aerosol (i.e., a condensation aerosol). Exemplary methods of heating include the passage of current through an electrical resistance element, absorption of electromagnetic radiation (e.g., microwave or laser light) and exothermic chemical reactions (e.g., exothermic salvation, hydration of pyrophoric materials, and oxidation of combustible materials). Heating of the substrate by conductive heating is also suitable. One exemplary heating source is described in U.S. patent application for SELF-CONTAINED HEATING UNIT AND DRUG-SUPPLY UNIT EMPLOYING SAME, U.S. Ser. No. 60/472,697 filed May 21, 2003. The description of the exemplary heating source disclosed therein, is hereby incorporated by reference.

Heat sources or devices that contain a chemically reactive material, which undergoes an exothermic reaction upon actuation, e.g., by a spark or heat element, such as a flashbulb type heater described in U.S. patent application for SELF-CONTAINED HEATING UNIT AND DRUG-SUPPLY UNIT EMPLOYING SAME, are also suitable. In particular, heat sources that generate heat by exothermic reaction, where the chemical "load" of the source is consumed in a period of between 50-500 msec or less are generally suitable, assuming good thermal coupling between the heat source and substrate.

In one method, the heating of the diuretic composition involves heating a thin film of the composition having a thickness between about 0.05 μm-20 μm to form a vapor. In yet other variations, the composition has a film thickness between about 0.5 μm-10 μm. Most typically, the film thickness vaporized is between 0.5 μm-5 μm.

In some variations, the diuretic condensation aerosol comprises at least 5% by weight of diuretic condensation aerosol particles. In other variations, the aerosol comprises at least 10%, 20%, 30%, 40%, 50%, 60%, or 75% by weight of diuretic condensation aerosol particles. In still other variations, the aerosol comprises at least 95%, 99%, or 99.5% by weight of diuretic condensation aerosol particles.

In some variations, the diuretic condensation aerosol particles comprise less than 10% by weight of a thermal degradation product. In other variations, the diuretic condensation aerosol particles comprise less than 5%, 1%, 0.5%, 0.1%, or 0.03% by weight of a thermal degradation product.

In some variations the diuretic condensation aerosol has a MMAD in the range of about 1-3 μm. In some variations the diuretic condensation aerosol has a MMAD in the range of 1-3.5 μm. In some variations the geometric standard deviation around the MMAD of the diuretic condensation aerosol particles is less than 3.0. In other variations, the geometric standard deviation around the MMAD of the diuretic condensation aerosol particles is less than 2.5, or less than 2.0.

The aerosol particles for administration can typically be formed using any of the describe methods at a rate of greater than $10^8$ inhalable particles per second. In some variations, the aerosol particles for administration are formed at a rate of greater than $10^9$ or $10^{10}$ inhalable particles per second. Similarly, with respect to aerosol formation (i.e., the mass of aerosolized particulate matter produced by a delivery device per unit time) the aerosol may be formed at a rate greater than 0.25 mg/second, grater than 0.5 mg/second, or greater than 1 or 2 mg/second.

Delivery Device

The delivery devices described herein for administering a diuretic condensation aerosol typically comprise an element for heating the diuretic composition to form a vapor, an element allowing the vapor to cool, thereby forming a condensation aerosol, and an element permitting a user to inhale the aerosol. The delivery device may be combined with a composition comprising a diuretic compound in unit dose form for use as a kit.

One suitable device is illustrated in FIG. 1. Delivery device 100 has a proximal end 102 and a distal end 104, a solid support 106, a power source 108, and a mouthpiece 110. In this depiction, solid support 106 also comprises a heating module. A diuretic composition is deposited on solid support 106. Upon activation of a user activated switch 114, power source 108 initiates heating of heating module (e.g., through ignition of combustible fuel or passage of current through a resistive heating element, etc.).

The diuretic composition vaporizes and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by a user.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e., "lock-out" feature). In addition, the device may further include a component to prevent use by unauthorized individuals, and a component to record dosing histories. These components may be used alone, or in combination with other components.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

Figure 2A:
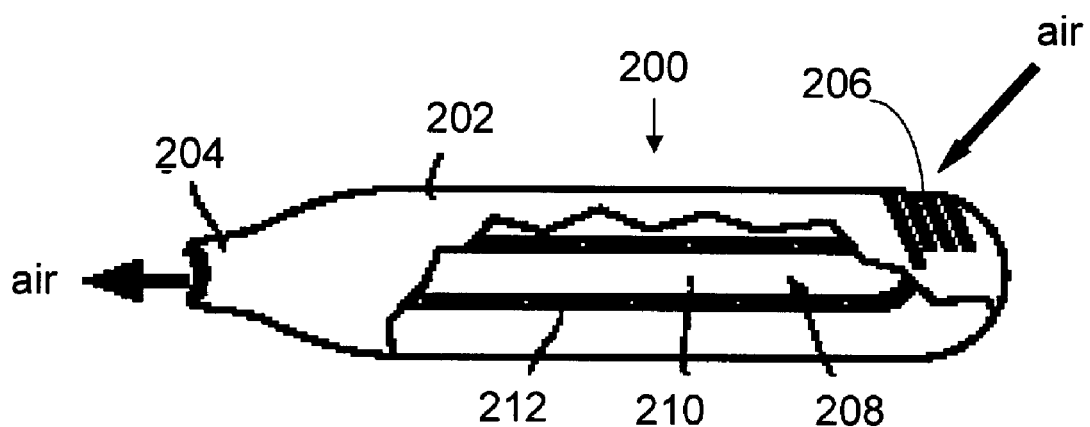
FIGS. 2A and 2B are illustrations of other exemplary devices that may be used to form and administer the aerosols described herein.
Figure 2B:
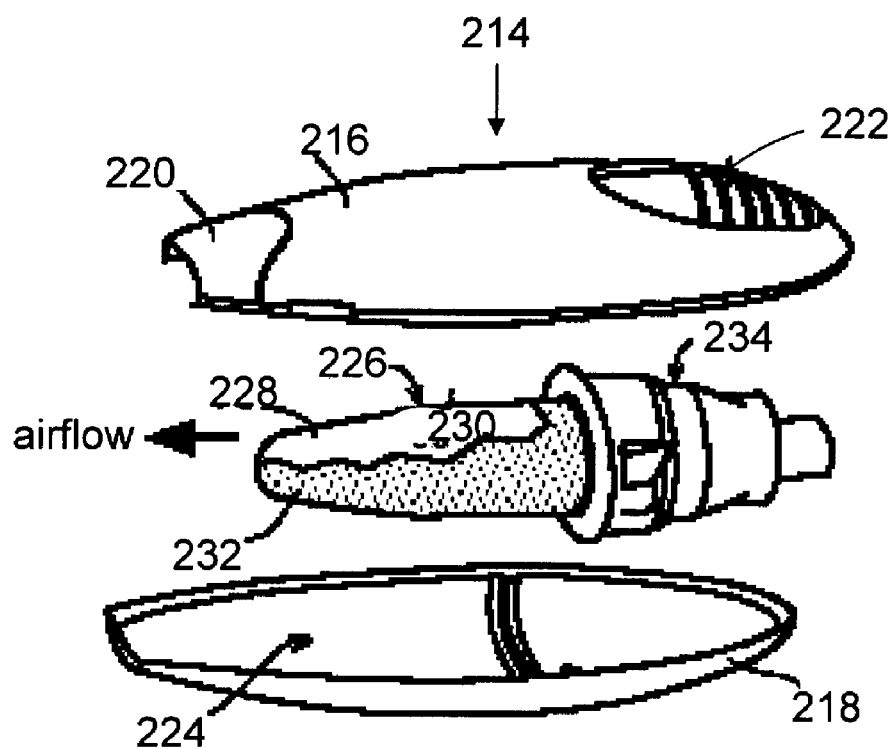

Other suitable devices for use with the aerosols described herein are shown in FIGS. 2A and 2B. As shown in FIG. 2A, there is a device 200 comprising an element for heating a diuretic composition to form a vapor, an element allowing the vapor to cool, thereby forming a condensation aerosol, and an element permitting a user to inhale the aerosol. Device 200 also comprises a housing 202 with a tapered end 204 for insertion into the mouth of a user. On the end opposite tapered end 204, the housing has one or more openings, such as slots 206, for air intake when a user places the device in the mouth and inhales a breath. Within housing 202 is a solid support 208, visible in the cut-away portion of the figure. At least a portion of the solid support is coated on a surface 210 with a film 212 of a diuretic composition.

Typically, the solid support 208 is heated to a temperature sufficient to vaporize all or a portion of the film 212, so that the diuretic composition forms a vapor that becomes entrained in a stream of air during inhalation. As noted above, heating of the solid support 208 may be accomplished using, for example, an electrically-resistive wire embedded or inserted into the substrate and connected to a battery disposed in the housing. The heating can be actuated, for example, with a button on the housing or via breath actuation, as is known in the art.

FIG. 2B shows another device that may be used to form and deliver the aerosols described herein. The device, 214 comprises an element for heating a diuretic composition to form a vapor, an element allowing the vapor to cool, thereby forming a condensation aerosol, and an element permitting a user to inhale the aerosol. The device also comprises an upper external housing member 216 and a lower external housing member 218 that fit together.

Shown in the depiction of FIG. 2B, the downstream end of each housing member is gently tapered for insertion into a user's mouth, as best seen on upper housing member 216 at downstream end 220. The upstream end of the upper and lower housing members are slotted, as seen best in the figure in the upper housing member at 222, to provide for air intake when a user inhales. The upper and lower housing members when fitted together define a chamber 224. Positioned within chamber 224 is a solid support 226, shown in a partial cutaway view.

As shown in FIG. 2B, the solid support shown there is of a substantially cylindrical configuration having a slight taper. However, as described above the solid support may be of any desirable configuration. At least a portion of the solid support surface 228 is coated with a diuretic composition film 230. Visible in the cutaway portion of the solid support is an interior region 232, which comprises a substance suitable to generate heat. The substance may be, for example, a solid chemical fuel, chemical reagents that mix exothermically, an electrically resistive wire, or the like. A power supply source, if needed for heating, and any necessary valving for the inhalation device may be contained in end piece 234.

The device may also include a gas-flow control valve disposed upstream of the solid support, for limiting gas-flow rate through the condensation region. The gas-flow valve may, for example, include an inlet port communicating with the chamber, and a deformable flap adapted to divert or restrict air flow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit airflow rate into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

The gas control valve could, for example, function to limit air drawn into the device to a preselected level, e.g., 15 L/minute. In this way, air flow for producing particles of a desired size may be preselected and produced. For example, once this selected airflow level is reached, additional air drawn into the device would create a pressure drop across the bypass valve, which in turn would accommodate airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced. Typically, the faster the airflow, the smaller the particles. Thus, to achieve smaller or larger particles, the gas velocity through the condensation region of the chamber may be altered by modifying the gas-flow control valve to increase or decrease the volumetric airflow rate. For example, to produce condensation particles in the size range of about 1-3.5 μm MMAD, a chamber having substantially smooth-surfaced walls would have a selected gas-flow rate in the range of 4-50 L/minute.

Additionally, as will be appreciated by one of skill in the art, particle size may be altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousands of an inch from the substrate surface. Particle size is discussed in more detail below.

Figure 3A:
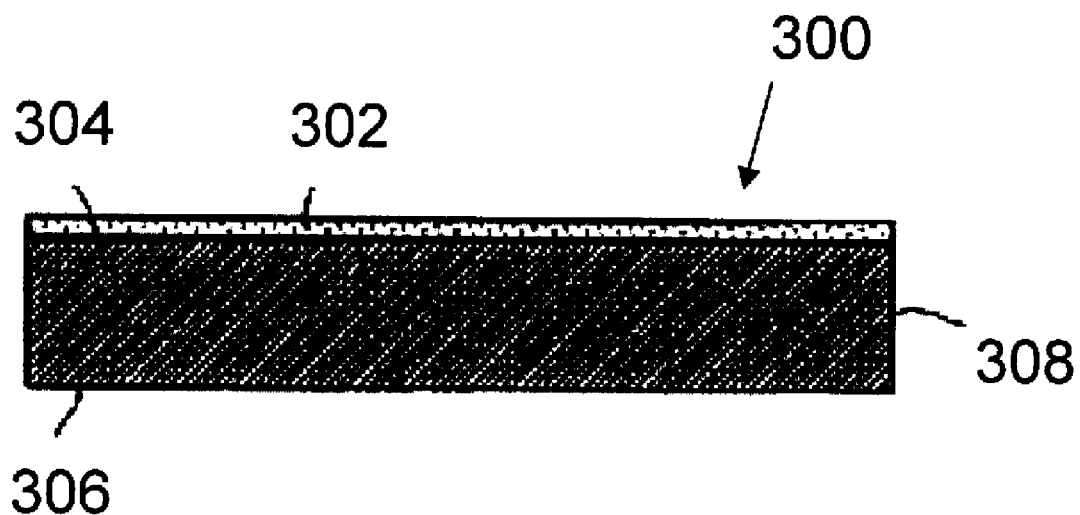
FIGS. 3A and 3B illustrate solid supports suitable for use with the devices and methods described herein.
Figure 3B:
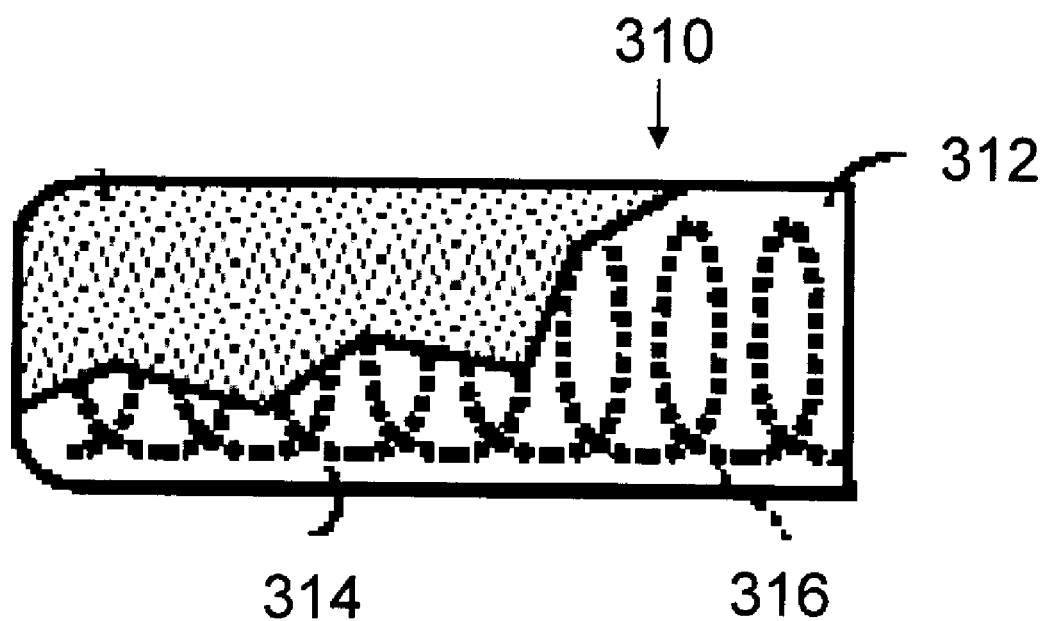

FIGS. 3A and 3B provide exploded views of solid supports that may be used in combination with the devices described herein. As shown in FIG. 3A, there is a solid support 300 having a diuretic composition coating 302 at least a portion of the upper surface 304. While the coating 302 is shown on upper surface 304 in FIG. 3A, it should be understood that it need not be so. Indeed, the coating may be placed on any suitable surface, such as surfaces 306 and 308.

FIG. 3B provides a perspective, cut-away view of another solid support 310 that may be used with the methods and devices herein described. As shown there, the solid support 310 comprises a cylindrically-shaped substrate 312. This substrate may be formed from a heat-conductive material, for example. The exterior surface 314 of substrate 312 is coated with a diuretic composition. As shown in the cut-away portion, there is a heating element 316 disposed in the substrate. The substrate can be hollow with a heating element inserted into the hollow space or solid with a heating element incorporated into the substrate.

The illustrative heating element shown in FIG. 3B is shown as an electrical resistive wire that produces heat when a current flows through it, but as noted above, a number of different heating methods and corresponding devices are acceptable. For example, acceptable heat sources can supply heat to the solid support at rates that rapidly achieve a temperature sufficient to completely vaporize the diuretic composition from the support surface. For example, heat sources that achieve a temperature of 200° C. to 500° C. within a period of 2 seconds, although it should be appreciated that the temperature chosen will be dependent upon the vaporization properties of the diuretic composition.

Diuretic Composition Film Thickness

Typically, the diuretic composition film coated on the solid support has a thickness of between about 0.05-20 μm, and typically a thickness between 0.1-15 μm. More typically, the thickness is between about 0.2-10 μm; even more typically, the thickness is between about 0.5-10 μm, and most typically, the thickness is between about 0.5-5 μm. The desirable film thickness for any given diuretic composition is typically determined by an iterative process in which the desired yield and purity of the condensation aerosol composition are selected or known.

For example, if the purity of the particles is less than that which is desired, or if the percent yield is less than that which is desired, the thickness of the drug film is adjusted to a thickness different from the initial film thickness. The purity and yield are then determined at the adjusted film thickness, and this process is repeated until the desired purity and yield are achieved. After selection of an appropriate film thickness, the area of substrate required to provide a therapeutically effective dose, is determined.

Figure 4:
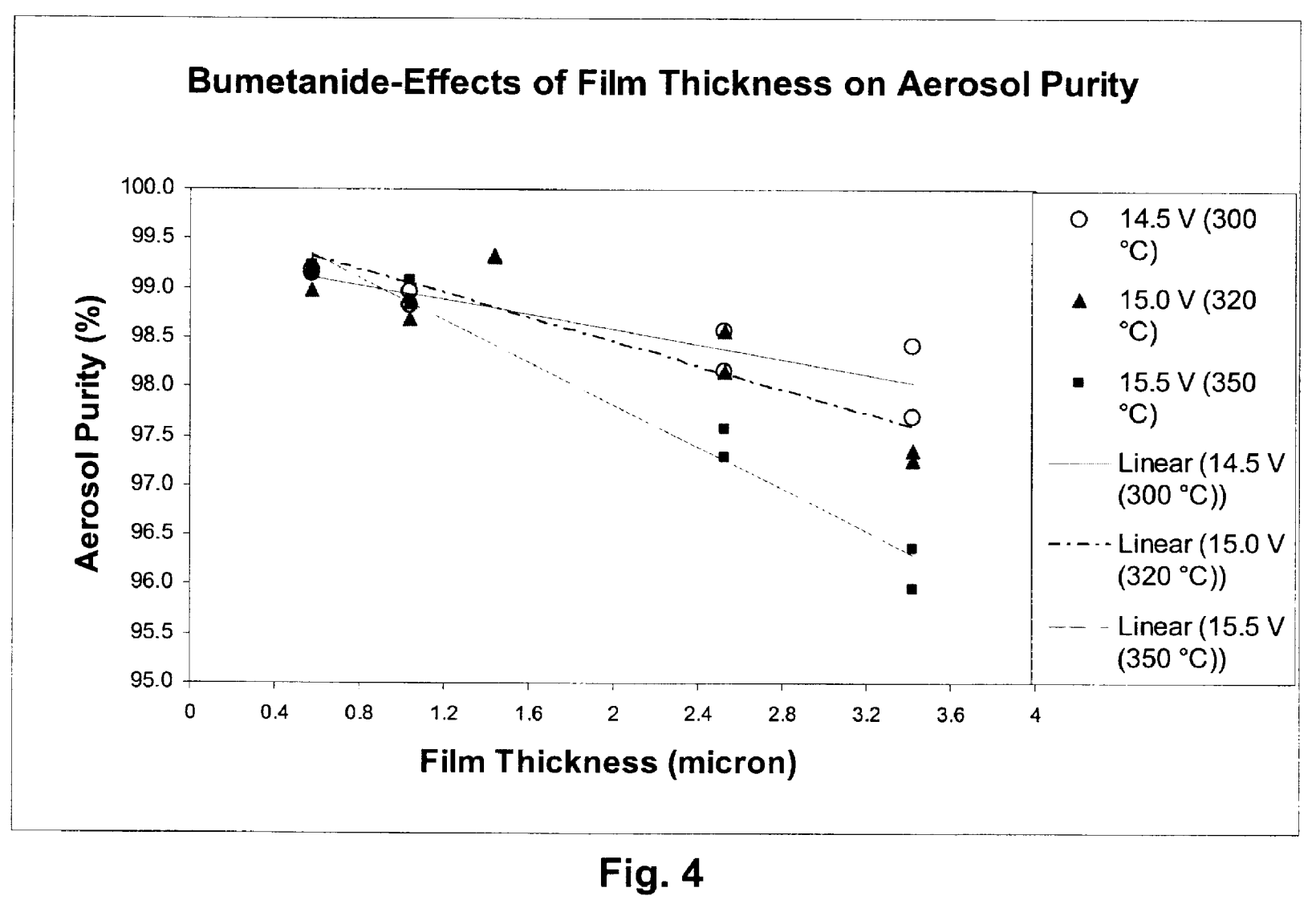

An example of how film thickness affects purity is depicted in FIG. 4 for the diuretic compound bumetanide.

Solid Support Surface Area

As noted above, the surface area of the solid support is selected such that it is sufficient to yield a therapeutically effective dose. The amount of diuretic compound required to provide a therapeutically effective dose is generally known in the art, and is discussed in more detail below. The substrate area may then be determined using the following equation:

$$\frac{\text{film thickness (cm)} \times \text{drug density (g/cm3)} \times \text{substrate area (cm2)} = \text{dose (g)}}{}$$

OR $$\text{substrate area (cm2)} = \text{dose (g)} / [\text{film thickness (cm)} \times \text{drug density (g/cm3)}]$$

The drug mass can be determined by weighing the substrate before and after formation of the drug film or by extracting the drug and measuring the amount analytically. Drug density can be determined experimentally by a variety of well known techniques, or may be found in the literature or in reference texts, such as in the CRC. An assumption of unit density is acceptable if an actual drug density is not known.

Dosage of Diuretic Containing Aerosols

The dose of a diuretic compound or compounds in aerosol form is generally no greater than twice the standard dose of the drug given orally. For instance, ethacrynic acid, bumetanide, muzolimine, torsemide, or tripamide are given at strengths of 25 mg to 50 mg, 0.5 mg to 2 mg, 40 mg to 150 mg, 5 mg to 100 mg, and 5 mg to 15 mg respectively for the treatment of edema. As aerosols, 10 mg to 100 mg of ethacrynic acid, 0.1 mg to 10 mg of bumetanide, 10 mg to 200 mg of muzolimine, 1 mg to 150 mg of torsemide, and 1 mg to 25 mg of tripamide are generally provided per inhalation for the same indication.

A dosage of a diuretic containing aerosol may be administered in a single inhalation or may be administered in more than one inhalation, such as a series of inhalations. Where the drug is administered as a series of inhalations, the inhalations are typically taken within an hour or less (dosage equals sum of inhaled amounts). When the drug is administered as a series of inhalations, a different amount may be delivered in each inhalation.

One can determine the appropriate dose of a diuretic containing aerosol to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human and they typically provide accurate extrapolation of tests results to humans. Initial dose levels for testing in humans are generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Particle Size

Efficient aerosol delivery to the lungs requires that the particles have certain penetration and settling or diffusional characteristics. Deposition in the deep lungs occurs by gravitational settling and requires particles to have an effective settling size, defined as mass median aerodynamic diameter (MMAD), typically between 1-3.5 µm. Typically, in order to produce particles having a desired MMAD, gas or air is passed over the solid support at a certain flow rate.

Typically, the higher the flow rate, the smaller the particles that are formed. Therefore, in order to achieve smaller or larger particles, the flow rate through the condensation region of the delivery device may be altered. This may be done, for example, by modifying a gas-flow control valve to increase or decrease the volumetric airflow rate. To illustrate, condensation particles in the size range 1-3.5 µm MMAD may be produced by selecting the gas-flow rate to be in a range of 4-50 L/minute.

Additionally, as will be appreciated by one of skill in the art, particle size may also be altered by modifying the cross-section of the chamber condensation region to increase or decrease linear gas velocity for a given volumetric flow rate. In addition, particle size may also be altered by the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within within a few thousands of an inch from the substrate surface.

Analysis of Diuretic Containing Aerosols

Purity of a diuretic containing aerosol may be determined using a number of different methods. It should be noted that when the term "purity" is used, it refers to the percentage of aerosol minus the percent byproduct produced in its formation. Byproducts for example, are those unwanted products produced during vaporization. For example, byproducts include thermal degradation products as well as any unwanted metabolites of the active compound or compounds. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of byproduct. Any suitable trap may be used. Suitable traps include filters, glass wool, impingers, solvent traps, cold traps, and the like. Filters are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard (s), an approach well known in the art.

In many cases, the structure of a byproduct may not be known or a standard for it may not be available. In such cases, one may calculate the weight fraction of the byproduct by assuming it has an identical response coefficient (e.g. for ultraviolet absorption detection, identical extinction coefficient) to the drug component or components in the diuretic composition. When conducting such analysis, byproducts present in less than a very small fraction of the drug compound, e.g. less than 0.2% or 0.1% or 0.03% of the drug compound, are typically excluded. Because of the frequent necessity to assume an identical response coefficient between drug and byproduct in calculating a weight percentage of byproduct, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis. In certain cases where analysis of the drug by UV are not viable, other analytical tools such as GC/MS or LC/MS may be used to determine purity.

It is possible that modifying the form of the drug may impact the purity of the aerosol obtained. Although not always the case, the free base or free acid form of the drug as opposed to the salt, generally results in either a higher purity or yield of the resultant aerosol. Therefore, in certain circumstances, it may be more desirable to use the free base or free acid forms of the compounds used. Similarly, it is possible that changing the gas under which vaporization of the composition occurs may also impact the purity.

Other Analytical Methods

Particle size distribution of a diuretic containing aerosol may be determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density may be determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density may be determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density may be determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi*D^3*\phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation may be determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation may be determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation may be determined, for example, by delivering a diuretic containing aerosol into a confined chamber via an inhalation device over a set period of time (e.g., 3 s). Where the aerosol is pure diuretic, the amount of drug collected in the chamber is measured as described above. The rate of drug aerosol formation is equal to the amount of diuretic collected in the chamber divided by the duration of the collection time. Where the diuretic containing aerosol comprises a pharmaceutically acceptable excipient, multiplying the rate of aerosol formation by the percentage of diuretic in the aerosol provides the rate of drug aerosol formation.

Methods of Treating Edema

Also described herein are methods for treating edema. Typically the methods comprise the step of administering a therapeutically effective amount of a diuretic condensation aerosol to a person with edema. Typically the step of administering the diuretic condensation aerosol comprises the step of administering an orally inhalable diuretic condensation aerosol to the person with edema.

The diuretic aerosol may be administered in a single inhalation, or in more than one inhalation, as described above. In some variations, the diuretic achieves a $C_{max}$ in 10 minutes or less after the step of administering the aerosol. In other variations, the diuretic achieves a $C_{max}$ in less than 5 minutes, less than 2 minutes, or less than 1 minute after the step of administering the aerosol.

The edema may be associated, at least in part, with any number of causes or maladies. For example, the edema may be associated with a cause selected from the group consisting of congestive heart failure, cirrhosis of the liver, poor blood circulation, lymphatic system failure, chronic nephritis, malnutrition, preeclampsia, use of birth control pills, premenstrual syndrome, sunburn, hypertension, Meniere's disease, glaucoma, cystic fibrosis, and an imbalance of sodium and potassium.

The diuretic condensation aerosol may comprise a diuretic composition as described above. The diuretic composition typically comprises at least one diuretic selected from the group consisting of bumetanide, ethacrynic acid, furosemide, muzolimine, spironolactone, torsemide, triamterene, tripamide, BG 9928, and BG 9719. In some variations, the diuretic is bumetanide. In some variations, the diuretic condensation aerosol has a MMAD in the range of about 1-3 μm. In some variations, the diuretic condensation aerosol has a MMAD in the range of 1-3.5 μm.

In some variations, the method for treating edema comprising the step of administering a therapeutically effective amount of a diuretic aerosol to a person with edema, wherein the diuretic aerosol comprises a diuretic compound and has a MMAD in the range of about 1-3 μm, and wherein a peak plasma level of at least 30 ng/mL of the diuretic compound is achieved within 10 minutes of administration. In some variations, the method comprises the steps of obtaining a weight measurement of the person with edema prior to the step of administering a therapeutically effective amount of a diuretic aerosol, and using that weight measurement to assess whether to administer a therapeutically effective amount of a diuretic aerosol.

Methods of Treating Congestive Heart Failure

Also described herein are methods for treating congestive heart failure using loop diuretics such as bumetanide, torsemide, ethacrynic acid, and furosemide, for reasons unrelated or in addition to the treatment of edema. Typically the methods comprise the step of administering a therapeutically effective amount of a loop diuretic condensation aerosol to a person with congestive heart failure. Typically the step of administering the diuretic condensation aerosol comprises the step of administering an orally inhalable loop diuretic condensation aerosol to the person with congestive heart failure.

The loop diuretic aerosol may be administered in a single inhalation, or in more than one inhalation, as described above. In some variations, the loop diuretic achieves a $C_{max}$ in 10 minutes or less after the step of administering the aerosol. In other variations, the loop diuretic achieves a $C_{max}$ in less than 5 minutes, less than 2 minutes, or less than 1 minute after the step of administering the aerosol.

In the treatment of congestive heart failure, the modulation of the vascular tone of arteries, arterioles, venuoles, and/or veins can be useful. When delivered with an appropriate absorption pharmacokinetics, in particular the absorption pharmacokinetics produced by inhalation delivery using the methods described herein, diuretics, in particular loop diuretics, may produce a useful relaxation of particular blood vessels. Such relaxation or vasodilation serves to ameliorate the symptoms of congestive heart failure. While such relaxation may be useful at any point in the course of treatment of congestive heart failure, it is of particular benefit in the treatment of congestive heart failure exacerbations, where a patient experiences increasing symptoms, generally including increasing shortness of breath. In such cases, inhalation of a loop diuretic may result in almost immediate improvement in such symptoms, even before substantial relief of edema occurs or in certain cases even unrelated to the treatment of edema.

The loop diuretic condensation aerosol may comprise a loop diuretic composition as described above. The diuretic composition typically comprises at least one loop diuretic selected from the group consisting of bumetanide, ethacrynic acid, furosemide, and torsemide. In some variations, the loop diuretic is bumetanide. In some variations, the loop diuretic condensation aerosol has a MMAD in the range of about 1-3 µm. In some variations, the loop diuretic condensation aerosol has a MMAD in the range of 1-3.5 µm.

In some variations, the method for treating congestive heart failure comprising the step of administering a therapeutically effective amount of a loop diuretic aerosol to a person with congestive heart failure, wherein the loop diuretic aerosol comprises a loop diuretic compound and has a MMAD in the range of about 1-3 µm, and wherein a peak plasma level of at least 30 ng/mL of the loop diuretic compound is achieved within 10 minutes of administration.

WORKING EXAMPLES

The following working examples are meant to be illustrative, and are in no way intended to limit the scope of the invention. Ethacrynic acid and bumetanide are commercially available from Sigma-Aldrich (www.sigma-aldrich.com).

Example 1A

Volatilization of Ethacrynic Acid

About 1.1 mg of ethacrynic acid (MW 303, melting point 122° C., oral dose 25 mg) was dip coated onto the stainless steel surface of a flashbar apparatus at a thickness of about 1.32 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 99.83% ethacrynic acid.

To obtain higher purity aerosols, one can coat a lesser amount of drug, yielding a thinner film to heat. A linear decrease in film thickness is associated with a linear decrease in impurities.

Example 1B

Volatilization of Ethacrynic Acid

About 1.01 mg of ethacrynic acid (MW 303, melting point 122° C., oral dose 25 mg) was dip coated onto the stainless steel surface of a flashbar apparatus at a thickness of about 1.21 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 99.57% ethacrynic acid.

Example 2

Volatilization of Bumetanide

About 1.09 mg of bumetanide (MW 364, melting point 231° C., oral dose 0.5 mg) was dip coated onto the stainless steel surface of a flashbar apparatus at a thickness of about 1.3 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 98.44% bumetanide.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 300 milliseconds. Generation of the thermal vapor was complete by 1200 milliseconds.

Example 3A

Volatilization of Spironolactone

About 0.71 mg of spironolactone (MW 417, melting point 135° C., oral dose 25 mg) was dip coated onto the stainless steel surface of a flashbar apparatus at a thickness of about 0.85 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 100% spironolactone.

Example 3B

Volatilization of Spironolactone

About 0.84 mg of spironolactone (MW 417, melting point 135° C., oral dose 25 mg) was dip coated onto the stainless steel surface of a flashbar apparatus at a thickness of about 1.01 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 100% spironolactone.

Example 4A

Volatilization of Triamterene

About 0.733 mg of triamterene (MW 253, melting point 316° C., oral dose 100 mg) was dissolved in 50 µl of 88% formic acid and dripped onto the stainless steel surface of a flashbar apparatus at a thickness of about 0.97 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 99.76% triamterene.

Example 4B

Volatilization of Triamterene

About 0.841 mg of triamterene (MW 253, melting point 316° C., oral dose 100 mg) was manually coated onto the stainless steel surface of a flashbar apparatus at a thickness of about 1.11 µm. (The flashbar is a cylinder 3.5 cm long and 1.3 cm in diameter consisting of a hollow tube of 0.005" thick stainless steel.) Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 100% triamterene.

PROPHETIC EXAMPLES

The following prophetic examples are meant to be illustrative, and are in no way intended to limit the scope of the invention. As noted above, bumetanide is commercially available from Sigma-Aldrich (www.sigma-aldrich.com).

Example 5

Inhalation Toxicology and Pharmacokinetic Study of Inhaled Aerosol Formulations of Bumetanide in the Beagle Dog This example is meant to illustrate one way in which toxicology and pharmacokinetic data may be investigated with respect to the bumetanide condensation aerosols described herein. Toxicology and pharmacokinetic data may be gathered by studying daily oropharyngeal inhalation of bumetanide condensation aerosols over a 14 day period using a beagle dog model.

Beagle dogs are purchased from Covance Research Product, Route 2, Box 113, Cumberland, Va. 23040 and are approximately 7-10 months of age and 6-12 kg at the onset of treatment. They are housed individually in stainless steel cages equipped with a bar-type floor and an automatic watering valve. Each cage is clearly labeled with a color-coded cage card indicating project, group, animal and tattoo number and sex. Each animal is uniquely identified by a permanent tattoo number and/or letter on ventral aspect of one pinna.

All animals have access to a standard certified pelleted commercial dog food (400 g—PMI Certified Dog Chow 5007: PMI Nutrition International Inc.) except during designated procedures. Municipal tap water which is softened, purified by reverse osmosis and exposed to ultraviolet light is freely available except during designated procedures. An acclimation period of approximately 3 weeks is allowed between animal receipt and the start of treatment in order to accustom the animals to the laboratory environment.

Before treatment initiation, all animals are weighed and assigned to treatment groups using a randomization procedure. Animals are assigned into the following groups: bumetanide high dose, bumetanide mid dose, bumetanide low dose, and vehicle control at 3 animals per sex per dose. The dose levels for bumetanide are generally approximately 0.1 mg/kg for the low dose group, 0.5 mg/kg for the mid dose group, and 2 mg/kg for the high dose group. The dose levels can be refined through an initial dose ranging toxicology study.

Animals are treated with the test aerosols using an oropharyngeal face mask fitted with inlet and outlet tubes. During treatment, animals are placed in a restraint sling. A mask that allows the inhalation of test material to dogs is used. The test article is generated by vaporizing bumetanide by heating to roughly 400° C. The bumetanide is an approximately 1 micron thick film coating on a stainless steel foil, which was deposited on the foil by dip coating the foil into a solution of bumetanide dissolved in organic solvent.

The resulting aerosol formed by the condensation of the vaporized bumetanide is introduced into a mixing chamber via pre-dried compressed air. The mixing chamber is operated under slight positive pressure maintained by means of a gate valve located in the exhaust line. A vacuum pump is used to exhaust the inhalation chamber at the required flow rate and draw the contaminated air (excess aerosol and expired air) through a purifying system consisting of a 5 μm coarse filter before expelling the air from the building. The resulting atmosphere is carried to the dog mask via a delivery tube.

The vehicle control group is exposed to predried compressed air passed through the drug-heating apparatus with the apparatus loaded with a clean stainless steel foil instead of a bumetanide-coated foil. Except for absence of drug, exposure is matched to the high dose bumetanide group, in terms of the air being passed through the operating and thus heating apparatus and the dogs breathing only through the dog masks, and the dogs being restrained and handled in the same manner.

To ensure that the doses are correct, prior to the start of the treatment each day, atmosphere characterization of the test article aerosol is performed. Analysis of the aerosol particle size distribution for each bumetanide dose is conducted using a Cascade Impactor. Typical mass median aerodynamic diameter and geometric standard deviation measured during the study are 1.5 μm±2. Actual mask output concentrations of aerosol are measured during each exposure day from a sampling port from the animal breathing zone.

The achieved dose of active ingredient (mg/kg/day) for each treatment level is determined as follows:

Achieved Dose of Active Ingredient=[$RMV$×Active Concentration×$T$×$D$]/$BW$

Where the achieved dose of the active ingredient is in mg/kg/day; the RMV (i.e., respiratory minute volume) is in L/min; the Active Concentration (i.e., chamber concentration of active ingredient determined by chemical analysis) is in mg/L; T (i.e., treatment time) is in minutes; D is the total aerosol deposition fraction, according to the particle size; and BW (i.e., mean body weight per sex per group from the regular body weight occasions during treatment) is in kg.

Dogs are treated with the bumetanide aerosol using the above approach to deliver the drug aerosol and compute the delivered dose. The exposure period required to deliver a dose is typically approximately 10 minutes. Plasma samples for pharmacokinetic analysis are collected on one or more treatment days. Samples are typically collected pre-dose, 2 minutes into dosing, and the end of dosing, 20 minutes post dose, 1 hour post dose, 3 hours post dose, 9 hours post dose, and 24 hours post dose. Samples are analyzed by an appropriate method such as LC/MS or LC/MS/MS to determine the pharmacokinetics of bumetanide absorption and elimination.

Treatment results in rapid increases in bumetanide peak plasma levels, which occur at the end of treatment (i.e., generally within 10 minutes, assuming a treatment duration of 10 minutes or less). Substantial drug blood levels are already obtained at the 2 minute time point. Peak plasma blood levels of bumetanide exceed 30 ng/mL in the low dose group, 100 ng/mL in the mid dose group, and 300 ng/mL in the high dose group. Plasma levels at two minutes exceed 10 ng/mL in the low dose group, 30 ng/mL in the mid dose group, and 100 ng/mL in the high dose group. Immediately following drug administration, an increase in urination is noted, which persists for an approximately 4 hour period following treatment. Food consumption is roughly normal in all animals, with the possible exception of the high dose bumetanide group.

Animals are necropsied on completion of the treatment period. In order to avoid autolytic change, a complete gross pathology examination of the carcass is conducted immediately on all animals. No treatment related findings are detected during necropsy for any of the animals. Histopathological examination of any gross lesions is conducted. Again, no treatment related findings are observed. In addition, histopathological examination of the larynx, trachea, mainstem bronchi, lungs including bronchi are conducted. No treatment related abnormalities are observed, with the possible exception of minor changes in airway, nose, or lung histology in the high dose group.

Example 6

Delivery of a Single Bolus Inhalation of Bumetanide Condensation Aerosol to Anesthetized and Intubated Beagle Dog A condensation aerosol generating apparatus consisting of a heat source and a bumetanide coated solid support is assembled. The bumetanide solid support has a surface area of approximately 10 cm$^2$ and an approximately 1 μm thick film of bumetanide coated on its surface, in order to provide a resulting bumetanide dose of condensation aerosol of approximately 1 mg. The heat source is capable of heating to at least 250° C., but not greater than 500° C. The assembly is capable of being initiated to generate condensation aerosol upon input of an electrical signal.

Three beagle dogs are catheterized in their femoral vein. Then the dogs receive a pre-anesthetic dose of acepromazine (0.2 mL), followed by anesthesia with 5% isoflurane about 15 minutes later. An endotracheal tube is positioned in the trachea, the cuff inflated and anesthesia maintained using 2% isoflurane in oxygen. Dogs are then placed into a holding sling and connected to a condensation aerosol generator by the endotracheal tube. A monitoring system is used to measure the inspiration and expiration of the dogs, which is controlled by mechanical ventilation.

The test animals are induced into a state of apnea using positive pressure hyperventilation to prevent spontaneous breathing from interrupting the aerosol delivery. The monitoring system is used to time aerosol generation so that it occurs in the first portion of the ventilator-controlled inhalation phase of breathing. The aerosol delivery breath is preceded by ventilator-controlled near complete exhalation. A large tidal volume (generally not exceeding 1 L, to avoid the risk of pneumothorax) is then used for the aerosol delivery breath, followed by a 3 s breath-hold to maximize alveolar delivery. Such a breathing pattern mimics that of a patient instructed to "exhale, and then take a deep breath." Patients are familiar with breathing in this pattern when having their lungs examined by a doctor using a stethoscope. The condensation aerosol generating device connected to the endotracheal tube is activated near the beginning of the aerosol delivery breath, delivering the condensation aerosol over approximately the first second or less of that breath.

Venous blood samples are obtained at 0.3, 1, 3, 10, 30, 60, 120, 240, and 480 minutes after dosing. Plasma drug concentrations are determined using established methods described in the literature for bumetanide. These analyses reveal a $T_{max}$ of less than 10 minutes, with the $T_{max}$ generally occurring at the 3 minute sample or the 1 minute sample. $C_{max}$ is greater than 30 ng/mL, typically greater than 100 ng/mL, and often approximately 500 ng/mL. Bioavailability of the condensation aerosol delivery is greater than 50% of intravenous delivery, and often greater than 75% of intravenous delivery.

Example 7

Phase I/II Clinical Trial of Bumetanide Condensation Aerosol

A condensation aerosol generating handheld device as illustratively described above, is coated with bumetanide so as to release a 0, 0.25, 0.5, 1, or 2 mg (depending on coating thickness) of bumetanide condensation aerosol over a period of less than 1 second following actuation of the device by patient inspiration.

For the Phase I clinical trial, normal volunteers generally in the 18 to 45 year age range and not suffering from serious pulmonary, renal or cardiovascular disease are recruited to participate in the study, explained the potential risks of bumetanide inhalation, and asked for their informed consent. Those consenting are enrolled in the study. For a Phase I/II or Phase II study, the normal volunteers are replaced by patients with edema. Such patients are likely to have serious cardiovascular or renal disease. Except for this difference, the patient volunteers are consented, enrolled, and treated similar to the normal volunteers, except additional safety monitoring may be required.

An intravenous catheter is placed. In addition, a foley catheter may be placed to enable minute by minute measurement of urine output. Urine output is generally monitored for a period of at least 2 hours prior to dosing.

Volunteers are then given a handheld device. They may or may not be trained in appropriate breathing technique for use of the device prior to receiving the device. Minimally, each volunteer is instructed to exhale fully, then place the device in his or her lips and take a long, deep inhalation which is held for several seconds prior to exhaling. The volunteer then uses the device, receiving the prescribed quantity of bumetanide condensation aerosol. The volunteer and the medical personnel conducting the study may be blinded as to the dose of drug, or as to whether the drug is replaced by placebo (i.e., a device loaded with 0 mg bumetanide).

Venous blood samples are obtained approximately at 0.3, 1, 3, 10, 30, 60, 120, 240, 360, 500, 750, and 1000 minutes after dosing. Plasma drug concentrations are determined using established methods described in the literature for bumetanide. These analyses reveal a $T_{max}$ of less than 10 minutes, with the $T_{max}$ generally occurring at the 3 minute sample or the 1 minute sample. Bioavailability of the condensation aerosol delivery is greater than 35% of intravenous delivery, and often greater than 55% of intravenous delivery.

The below table provides illustrative anticipated $C_{max}$ values at different doses:

| Dose | $C_{max}$ typically greater than | Most typical $C_{max}$ greater than |
|---|---|---|
| 0.25 mg | 2.7 ng/mL | 25 ng/mL |
| 0.5 mg | 5 ng/mL | 50 ng/mL |
| 1 mg | 10 ng/mL | 100 ng/mL |
| 2 mg | 20 ng/mL | 200 ng/mL |

After inhalation of the condensation aerosol, an increase in urine output is noted almost immediately. For patients treated with 1 mg or 2 mg of bumetanide and having a foley catheter in place, an increase in urine output is frequently detectable with 10 minutes, or at most 20 minutes of condensation aerosol inhalation. For patients receiving lower doses or not having a foley catheter in place, increases in urine output also occur almost immediately but may be more difficult to detect.

Example 8

Determination of Whether Aerosol Delivery of Loop Diuretic is Therapeutically Indicated by Patient Self-Weighing at Home A female patient of 70 years with a history of congestive heart failure (e.g., New York Heart Association grade III), is instructed to weigh herself on a daily basis. Records of the patient's weight reveal that, when the patient feels relatively good, her weight is within 1 kg of her 80 kg base weight upon weighing in the morning prior to eating. Records further reveal that a weight gain of over 1 kg to greater than 81 kg is associated with increased symptoms of difficulty in walking. Yet further weight gain is associated with shortness of breath at rest. The patient is instructed to call her medical provider whenever she measures her weight (on an empty stomach) at above 81 kg. The medical provider reviews the patient's history and symptoms by telephone, focusing on recent diet (e.g., increased salt intake), symptoms of edema, difficulty breathing, and any symptoms of more serious illness. If the patient seems to be acutely decompensating due to edema, the patient is instructed to take a 2 mg dose of the bumetanide aerosol and immediately seek medical aid. If the patient seems to have a minor increase in edema, she is instructed to take a 1 mg dose of the bumetanide aerosol.

Example 9

Determination of Whether Aerosol Delivery of Loop Diuretic is Therapeutically Indicated by Weighing of Patient in a Medical Office A male patient of 52 years with a history of congestive heart failure (e.g., New York Heart Association grade IV), experiences increasing shortness of breath at rest and decides to seek medical assistance. Upon reaching his doctor's office, the patient's vital signs are measured and found to be normal except for mild tachypnea. There is no fever. The patient is weighed and his weight compared to last visit, which was a routine visit not during a congestive heart failure exacerbation. His weight has increased by 3 kg. The patient is given a condensation aerosol dose of 1 mg bumetanide. Within 30 minutes, shortness of breath improves and the patient is able to go home.

Example 10

Clinical Trial of the Efficacy of Bumetanide Condensation Aerosol in Congestive Heart Failure Exacerbations A condensation aerosol generating handheld device as illustratively described above, is coated with bumetanide so as to release a 0, 0.5, 1, or 2 mg (depending on coating thickness) of bumetanide condensation aerosol over a period of less than 1 second following actuation of the device by patient inspiration.

For the clinical trial, patients presenting to the emergency department with a history of congestive heart failure of New York Heart Association grade II or above with symptoms of a congestive heart failure exacerbation including a subjective sensation of shortness of breath, increased respiratory rate (>20 per minute) and/or poor oxygen saturation (<95%) when breathing room air, but not in such severe distress as to require immediate treatment, are recruited to participate in the study, explained the potential risks of bumetanide inhalation, and asked for their informed consent. Those consenting are enrolled in the study and randomized to receive a particular bumetanide dose.

Patients are then given a handheld device. They may or may not be trained in appropriate breathing technique for use of the device prior to receiving the device. Minimally, each patient is instructed to exhale fully, then place the device in his or her lips and take a long, deep inhalation which is held for several seconds prior to exhaling. The patient then uses the device, receiving the prescribed quantity of bumetanide condensation aerosol. The patient and the medical personnel conducting the study are blinded as to the dose of drug, or as to whether the drug is replaced by placebo (i.e., a device loaded with 0 mg bumetanide).

After inhalation of the condensation aerosol, an improvement in the congestive heart failure exacerbation is noted almost immediately, in general at a similar time as the first onset of diuretic effect but preceding clinically relevant diuresis. Inhalation of the condensation aerosol results in a clinically relevant reduction in shortness of breath and associated respiratory measures such as oxygen saturation when breathing room air and respiratory rate, compared to inhalation of placebo. Assuming enrollment of a sufficient patient sample, statistically significant effects at the p<0.05 level are obtained for inhaled drug vs. inhaled placebo within 20 minutes or less after inhalation.

While the present invention has been described with reference to one or more particular variations, those skilled in the art will recognize that many changes may be made hereto without departing from the spirit and scope of the devices and methods herein described and claimed.

What we claim is:

1. A condensation aerosol for delivery wherein the condensation aerosol is formed by heating a film containing a drug, to produce a vapor of the drug, and condensing the vapor to form a condensation aerosol characterized by less than 10% drug degradation products by weight, and a MMAD of less than 5 microns, wherein the drug is selected from the group consisting of bumetanide, ethacrynic acid, furosemide, muzolimine, spironolactone, torsemide, triamterene, tripamide, BG 9928 and BG 9719.

2. The condensation aerosol of claim 1, wherein the film has a thickness between 0.05 and 20 microns.

3. The condensation aerosol of claim 2, wherein the film has a thickness between 0.2 and 10 microns.

4. The condensation aerosol of claim 1, wherein the condensation aerosol is characterized by a MMAD of less than 3 microns.

5. The condensation aerosol of claim 1, wherein the condensation aerosol is characterized by a MMAD of 1 to 3.5 microns.

6. The condensation aerosol of claim 1, wherein the condensation aerosol is characterized by less than 5% drug degradation products by weight.

7. The condensation aerosol of claim 6, wherein the condensation aerosol is characterized by less than 2.5% drug degradation products by weight.

8. The condensation aerosol of claim 6, wherein the condensation aerosol is characterized by an MMAD of 1 to 3.5 microns and wherein the drug is bumetanide.

9. The condensation aerosol of claim 1, wherein the solid support is a metal foil.

10. The condensation aerosol of claim 1, wherein the drug is bumetanide.

11. The condensation aerosol of claim 1, wherein the drug is ethacrynic acid.

12. The condensation aerosol of claim 1, wherein the drug is furosemide.

13. The condensation aerosol of claim 1, wherein the drug is muzolimine.

14. The condensation aerosol of claim 1, wherein the drug is spironolactone.

15. The condensation aerosol of claim 1, wherein the drug is torsemide.

16. The condensation aerosol of claim 1, wherein the drug is triamterene.

17. The condensation aerosol of claim 1, wherein the drug is tripamide.

18. The condensation aerosol of claim 1, wherein the drug is BG 9928.

19. The condensation aerosol of claim 1, wherein the drug is BG 9719.

20. A method of producing a drug in an aerosol form comprising:
  a. heating a film containing the drug to produce a vapor of the drug, and
  b. providing an air flow through the vapor to form a condensation aerosol characterized by less than 10% drug degradation products by weight, and a MMAD of less than 5 microns, wherein the drug is selected from the group consisting of bumetanide, ethacrynic acid, furosemide, muzolimine, spironolactone, torsemide, triamterene, tripamide, BG 9928 and BG 9719.

21. The method of claim 20, wherein the condensation aerosol is formed at a rate greater than $10^9$ particles per second.

22. The method of claim 21, wherein the condensation aerosol is formed at a rate greater than $10^{10}$ particles per second.

23. The method of claim 20, wherein the condensation aerosol is characterized by a MMAD of less than 3 microns.

24. The method of claim 20, wherein the condensation aerosol is characterized by a MMAD of 1 to 3.5 microns.

25. The method of claim 20, wherein the condensation aerosol is characterized by less than 5% drug degradation products by weight.

26. The method of claim 25, wherein the condensation aerosol is characterized by less than 2.5% drug degradation products by weight.

27. The method of claim 25, wherein the condensation aerosol is characterized by a MMAD of 1 to 3.5 microns and wherein the drug is bumetanide.

28. The method of claim 24, wherein the solid support is a metal foil.

29. The method of claim 24, wherein the drug is bumetanide.

30. The method of claim 24, wherein the drug is ethacrynic acid.

31. The method of claim 24, wherein the drug is furosemide.

32. The method of claim 24, wherein the drug is muzolimine.

33. The method of claim 24, wherein the drug is spironolactone.

34. The method of claim 24, wherein the drug is torsemide.

35. The method of claim 24, wherein the drug is triamterene.

36. The method of claim 24, wherein the drug is tripamide.

37. The method of claim 24, wherein the drug is BG 9928.

38. The method of claim 24, wherein the drug is BG 9719.

39. The method of claim 20, wherein the film has a thickness between 0.05 and 20 microns.

40. The method of claim 39, wherein the film has a thickness between 0.2 and 10 microns.

41. A method of treating edema in a patient comprising administering to the patient a therapeutic amount of a drug condensation aerosol by inhalation, wherein the condensation aerosol is formed by heating a film containing the drug to produce a vapor of the drug, and condensing the vapor to form a condensation aerosol characterized by less than 10% drug degradation products by weight, and a MMAD of less than 5 microns, wherein the drug is selected from the group consisting of bumetanide, ethacrynic acid, furosemide, muzolimine, spironolactone, torsemide, triamterene, tripamide, BG 9928 and BG 9719.

42. The method of claim 41, wherein the condensation aerosol is characterized by a MMAD of less than 3 microns.

43. The method of claim 41, wherein the condensation aerosol is characterized by a MMAD of 1 to 3.5 microns.

44. The method of claim 41, wherein the condensation aerosol is characterized by less than 5% drug degradation products be weight and wherein the drug is bumetanide.

45. The method of claim 41, wherein peak plasma drug concentration is reached in less than 0.1 hours.

46. The method of claim 41, wherein the condensation aerosol is formed at a rate greater than 0.5 mg/second.

47. The method of claim 41, wherein at least 50% by weight of the condensation aerosol is amorphous in form.

48. The method of claim 41, wherein the therapeutic amount of a drug condensation aerosol comprises between 0.1 mg and 10 mg of bumetanide delivered in a single inspiration.

49. The method of claim 41, wherein the therapeutic amount of a drug condensation aerosol comprises between 10 mg and 100 mg of ethacrynic acid delivered in a single inspiration.

50. The method of claim 41, wherein the therapeutic amount of a drug condensation aerosol comprises between 10 mg and 200 mg of muzolimine delivered in a single inspiration.

51. The method of claim 41, wherein the therapeutic amount of a drug condensation aerosol comprises between 1 mg and 150 mg of torsemide delivered in a single inspiration.

52. The method of claim 41, wherein the therapeutic amount of a drug condensation aerosol comprises between 1 mg and 25 mg of tripamide delivered in a single inspiration.

53. The method of claim 41, wherein the therapeutic amount of a drug condensation aerosol comprises between 1 mg and 25 mg of delivered in a single inspiration.

54. The method of claim 41, wherein the film has a thickness between 0.05 and 20 microns.

55. The method of claim 54, wherein the film has a thickness between 0.2 and 10 microns.

56. A method of treating congestive heart failure in a patient comprising administering to the patient a therapeutic amount of a drug condensation aerosol by inhalation, wherein the condensation aerosol is formed by heating a film containing the drug to produce a vapor of the drug, and condensing the vapor to form a condensation aerosol characterized by less than 10% drug degradation products by weight, and a MMAD of less than 5 microns, wherein the drug is selected from the group consisting of bumetanide, ethacrynic acid, furosemide and torsemide.

57. The method of claim 56, wherein the condensation aerosol is characterized by a MMAD of less than 3 microns.

58. The method of claim 56, wherein the condensation aerosol is characterized by a MMAD of 1 to 3.5 microns.

59. The method of claim 58, wherein the condensation aerosol is characterized by less than 5% drug degradation products by weight and wherein the drug is bumetanide.

60. The method of claim 56, wherein peak plasma drug concentration is reached in less than 0.1 hours.

61. The method of claim 56, wherein the condensation aerosol is formed at a rate greater than 0.5 mg/second.

62. The method of claim 56, wherein at least 50% by weight of the condensation aerosol is amorphous in form.

63. The method of claim 56, wherein the therapeutic amount of a drug condensation aerosol comprises between 0.1 mg and 10 mg of bumetanide delivered in a single inspiration.

64. The method of claim 56, wherein the therapeutic amount of a drug condensation aerosol comprises between 10 mg and 100 mg of ethacrynic acid delivered in a single inspiration.

65. The method of claim 56, wherein the therapeutic amount of a drug condensation aerosol comprises between 10 mg and 200 mg of muzolimine delivered in a single inspiration.

66. The method of claim 56, wherein the therapeutic amount of a drug condensation aerosol comprises between 1 mg and 150 mg of torsemide delivered in a single inspiration.

67. The method of claim 56, wherein the therapeutic amount of a drug condensation aerosol comprises between 1 mg and 25 mg of triamterene delivered in a single inspiration.

68. The method of claim 56, wherein the film has a thickness between 0.05 and 20 microns.

69. The method of claim 68, wherein the film has a thickness between 0.2 and 10 microns.

70. A method of administering a drug to a patient comprising administering to the patient a therapeutic amount of a drug condensation aerosol by inhalation, wherein the drug condensation aerosol is formed by heating a film containing the drug to produce a vapor of the drug, and condensing the vapor to form a condensation aerosol characterized by less than 10% drug degradation products by weight, and a MMAD of less than 5 microns, wherein the drug is selected from the group consisting of bumetanide, ethacrynic acid, furosemide, muzolimine, spironolactone, torsemide, triamterene, tripamide, BG 9928 and BG 9719.

71. The method of claim 70, wherein the drug is bumetanide.

72. The method of claim 70, wherein the drug is ethacrynic acid.

73. The method of claim 70, wherein the drug is furosemide.

74. The method of claim 70, wherein the drug is muzolimine.

75. The method of claim 70, wherein the drug is spironolactone.

76. The method of claim 70, wherein the drug is torsemide.

77. The method of claim 70, wherein the drug is triamterene.

78. The method of claim 70, wherein the drug is tripamide.

79. The method of claim 70, wherein the drug is BG 9928.

80. The method of claim 70, wherein the drug is BG 9719.

81. The method of claim 70, wherein the film has a thickness between 0.05 and 20 microns.

82. The method of claim 81, wherein the film has a thickness between 0.2 and 10 microns.

83. A kit for delivering a drug condensation aerosol comprising:

a. a film containing the drug, wherein the drug is selected from the group consisting of bumetanide, ethacrynic acid, furosemide, muzolimine, spironolactone, torsemide, triamterene, tripamide, BG 9928 and BG 9719, and b. a device for providing the condensation aerosol, wherein the condensation aerosol is formed by heating the film to produce a vapor of the drug, and condensing the vapor to form a condensation aerosol characterized by less than 10% drug degradation products by weight, and a MMAD of less than 5 microns.

84. The kit of claim 83, wherein the device comprises:

a. a flow through enclosure containing the solid support, b. a power source that can be activated to heat the solid support, and c. at least one portal through which air can be drawn by inhalation, wherein activation of the power source is effective to produce a vapor of the drug, and drawing air through the enclosure is effective to condense the vapor to form the condensation aerosol.

85. The kit of claim 84, wherein the heat for heating the solid support is generated by an exothermic chemical reaction.

86. The kit of claim 85, wherein the exothermic chemical reaction is oxidation of combustible materials.

87. The kit of claim 84, wherein the heat for heating the solid support is generated by passage of current through an electrical resistance element.

88. The kit of claim 84, wherein the solid support has a surface area dimensioned to accommodate a therapeutic dose of the drug.

89. The kit of claim 83, wherein peak plasma drug concentration is reached in less than 0.1 hours.

90. The kit of claim 83, further including instructions for use.

91. The kit of claim 83, wherein the condensation aerosol is characterized by a MMAD of less than 3 microns.

92. The kit of claim 83, wherein the condensation aerosol is characterized by a MMAD of 1 to 3.5 microns.

93. The kit of claim 83, wherein the condensation aerosol is characterized by less than 5% drug degradation products be weight and wherein the drug is bumetanide.

94. The kit of claim 83, wherein the drug is bumetanide.

95. The kit of claim 83, wherein the drug is ethacrynic acid.

96. The kit of claim 83, wherein the drug is furosemide.

97. The kit of claim 83, wherein the drug is muzolimine.

98. The kit of claim 83, wherein the drug is spironolactone.

99. The kit of claim 83, wherein the drug is torsemide.

100. The kit of claim 83, wherein the drug is triamterene.

101. The kit of claim 83, wherein the drug is tripamide.

102. The kit of claim 83, wherein the drug is BG 9928.

103. The kit of claim 83, wherein the drug is BG 9719.

104. The kit of claim 83, wherein the solid support has a surface to mass ratio of greater than 1 $cm^2$ per gram.

105. The kit of claim 83, wherein the solid support has a surface to volume ratio of greater than 100 per meter.

106. The kit of claim 83, wherein the solid support is a metal foil.

107. The kit of claim 106, wherein the metal foil has a thickness of less than 0.25 mm.

108. The kit of claim 83, wherein the film has a thickness between 0.05 and 20 microns.

109. The kit of claim 108, wherein the film has a thickness between 0.2 and 10 microns.

* * * * *